(12) United States Patent
Stella et al.

(10) Patent No.: US 9,034,895 B2
(45) Date of Patent: May 19, 2015

(54) COMPOSITION AND METHODS FOR TREATING GLIOBLASTOMA

(75) Inventors: Nephi Stella, Seattle, WA (US); Toni Kline, Seattle, WA (US)

(73) Assignee: University of Washington Through its Center for Commercialization, Seattle, WA (US)

( * ) Notice: Subject to any disclaimer, the term of this patent is extended or adjusted under 35 U.S.C. 154(b) by 88 days.

(21) Appl. No.: 13/818,026

(22) PCT Filed: Aug. 22, 2011

(86) PCT No.: PCT/US2011/048594
§ 371 (c)(1),
(2), (4) Date: Mar. 21, 2013

(87) PCT Pub. No.: WO2012/024670
PCT Pub. Date: Feb. 23, 2012

(65) Prior Publication Data
US 2013/0197026 A1    Aug. 1, 2013

Related U.S. Application Data

(60) Provisional application No. 61/375,704, filed on Aug. 20, 2010.

(51) Int. Cl.
| | | |
|---|---|---|
| C07D 401/04 | (2006.01) | |
| C07D 209/12 | (2006.01) | |
| C07D 219/12 | (2006.01) | |
| C07D 401/06 | (2006.01) | |
| C07D 403/06 | (2006.01) | |
| C07D 471/04 | (2006.01) | |
| C07D 471/10 | (2006.01) | |
| G01N 33/94 | (2006.01) | |

(52) U.S. Cl.
CPC ............ *C07D 401/04* (2013.01); *C07D 209/12* (2013.01); *C07D 219/12* (2013.01); *C07D 401/06* (2013.01); *C07D 403/06* (2013.01); *C07D 471/04* (2013.01); *C07D 471/10* (2013.01); *G01N 33/94* (2013.01)

(58) Field of Classification Search
CPC ............................ C07D 471/04; A61K 31/407
USPC .............................................. 546/94; 514/294
See application file for complete search history.

(56) References Cited

U.S. PATENT DOCUMENTS

| 5,013,837 A | 5/1991 | Ward et al. |
| 6,013,648 A | 1/2000 | Rinaldi et al. |
| 7,144,913 B2 * | 12/2006 | Wang et al. .................. 514/411 |
| 2005/0009903 A1 | 1/2005 | Martin et al. |

FOREIGN PATENT DOCUMENTS

WO        02094830     * 11/2002

OTHER PUBLICATIONS

Bouaboula, et al. (1995). Stimulation of cannabinoid receptor CB1 induces krox-24 expression in human astrocytoma cells. The Journal of Biological Chemistry, 270, 13973-13980.
Bouaboula, et al. (1996). Signaling pathway associated with stimulation of CB2 peripheral cannabinoid receptor. European Journal of Biochemistry, 237, 704-711.
Breivogel, et al. (2001). Evidence for a new G protein-coupled cannabinoid receptor in mouse brain. Mol Pharmacol, 60(1), 155-163.
Caron, et al. (1993). Catecholamine receptors: structure, function, and regulation. Recent Prog Horm Res, 48, 277-290.
Carracedo, et al. (2006). The stress-regulated protein p8 mediates cannabinoid-induced apoptosis of tumor cells. Cancer Cell, 9(4), 301-312. doi: S1535-6108(06)00085-7 [pii] 10.1016/j.ccr.2006.03.005.
Ellert-Miklaszewska, et al. (2005). Cannabinoids down-regulate PI3K/Akt and Erk signalling pathways and activate proapoptotic function of Bad protein. Cell Signal, 17(1), 25-37. doi: 10.1016/j.cellsig.2004.05.011 S0898656804001007 [pii].
Fowler, et al. (2003). Inhibition of C6 glioma cell proliferation by anandamide, 1-arachidonoylglycerol, and by a water soluble phosphate ester of anandamide: variability in response and involvement of arachidonic acid. Biochem Pharmacol, 66(5), 757-767. doi: S0006295203003927 [pii].
Freedman, et al. (1996). Desensitization of G protein-coupled receptors. Recent Prog Horm Res, 51, 319-351; discussion 352-313.
Galve-Roperh, et al. (2000). Anti-tumoral action of cannabinoids: involvement of sustained ceramide accumulation and extracellular signal-regulated kinase activation. Nature Medicine, 6, 313-319.
Gewirtz, (1999). A critical evaluation of the mechanisms of action proposed for the antitumor effects of the anthracycline antibiotics adriamycin and daunorubicin. Biochem Pharmacol, 57(7), 727-741. doi: S0006295298003074 [pii].
Gudermann, et al. (1995). Receptors and G proteins as primary components of transmembrane signal transduction. Part 1. G-protein-coupled receptors: structure and function. J Mol Med (Berl), 73(2), 51-63.

(Continued)

*Primary Examiner* — Rita Desai
(74) *Attorney, Agent, or Firm* — McDonnell Boehnen Hulbert & Berghoff LLP

(57) ABSTRACT

The disclosure provides methods of treating glioblastoma, methods of screening for compounds that treat glioblastoma, and pharmaceutical compositions useful the treatment of glioblastoma.

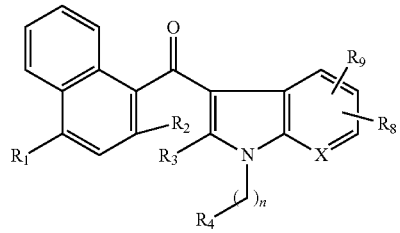

10 Claims, 7 Drawing Sheets

(56) References Cited

OTHER PUBLICATIONS

Guzman, et al., 1998. "Early postoperative complications after coronary artery bypass grafting at the Cardiovascular Center of Puerto Rico and the Caribbean," PR Health Sci J, 17(4): 353-7.

Hajos, et al. (2001). Novel cannabinoid-sensitive receptor mediates inhibition of glutamatergic synaptic transmission in the hippocampus. Neuroscience, 106(1), 1-4.

Held-Feindt, et al. (2006). Cannabinoid receptors in human astroglial tumors. J Neurochem, 98(3), 886-893.

Hillard, et al., (1995) "Characterization of ligand binding to the cannabinoid receptor of rat brain membranes using a novel method: application to anandamide," J Neurochem, 64:677-683.

Jacobsson, et al. (2001). Inhibition of rat C6 glioma cell proliferation by endogenous and synthetic cannabinoids. Relative involvement of cannabinoid and vanilloid receptors. J Pharmacol Exp Ther, 299(3), 951-959.

Kandemirli, et al., (2002) "Structure-activity relationships investigation in a mixed series of cannabinoids an electronic-topological approach," Drug Research, 53(10): 731-739.

Kogan, et al. (2004). Synthesis and antitumor activity of quinonoid derivatives of cannabinoids. J Med Chem, 47(15), 3800-3806.

Maccarrone, et al. (2002). Binding, degradation and apoptotic activity of stearoylethanolamide in rat C6 glioma cells. Biochemical Journal, 366, 137-144.

Massi, et al. (2006). The non-psychoactive cannabidiol triggers caspase activation and oxidative stress in human glioma cells. Cell Mol Life Sci, 63(17), 2057-2066. doi: 10.1007/s00018-006-6156-x.

Massi, et al. (2004). Antitumor effects of cannabidiol, a nonpsychoactive cannabinoid, on human glioma cell lines. J Pharmacol Exp Ther, 308(3), 838-845.

McAllister, et al., (2005) "Cannabinoids selectively inhibit proliferation and induce death of cultures human glioblastoma multiforme cells," Jounral of Neuro-oncology, 74(1):31-40.

Sagan, et al., (1997), High affinity binding of [3H]propionyl-[Met(O2)11]substance P(7-11), a tritiated septide-like peptide, in Chinese hamster ovary cells expressing human neurokinin-1 receptors and in rat submandibular glands, Mol Pharmacol, 52(1):120-7.

Salazar, et al. (2009). Cannabinoid action induces autophagy-mediated cell death through stimulation of ER stress in human glioma cells. J Clin Invest, 119(5), 1359-1372.

Sánchez, et al. (2001). Inhibition of glioma growth In Vivo by selective activation of the CB2 cannabinoid receptor. Cancer Res, 61, 5784-5789.

Sánchez, et al. (1998). Ð 9-tetrahydrocannabinol induces apoptosis in C6 glioma cells. FEBS letters, 436, 6-10.

Stark, et al. (1997). Binding of aminoalkylindoles to noncannabinoid binding sites in NG108-15 cells. Cell Mol Neurobiol, 17(5), 483-493.

Vaccani, et al. (2005). Cannabidiol inhibits human glioma cell migration through a cannabinoid receptor-independent mechanism. Br J Pharmacol, 144(8), 1032-1036. doi: 0706134 [pii] 10.1038/sj.bjp.0706134.

Yamada, et al., (1996) "(Aminoalkyl)iodle isothiocyanates as potential electrophilic affinity ligands for the brain cannabinoid receptor," Journal of Medicinal Chemistry, 39(10):1967-1974.

Written Opinion of International Searching Authority for PCT/US2011/048594, mailed Mar. 7, 2013.

* cited by examiner a.

b.

COMPOSITION AND METHODS FOR TREATING GLIOBLASTOMA

CROSS-REFERENCES TO RELATED APPLICATIONS

This application is a U.S. national phase of International Application No. PCT/US11/48594 filed on Aug. 22, 2011, which claims benefit of U.S. Provisional Application Ser. No 61/375,704, filed Aug. 20, 2010, both of which are incorporated by reference herein in their entirety.

STATEMENT REGARDING FEDERALLY SPONSORED RESEARCH

This invention was made with government support under under NIH RO1 DA021285. The government has certain rights.

BACKGROUND

1. Field of the Disclosure

The disclosure relates to methods and pharmaceutical compositions for treating brain tumors, and methods of screening for compounds that provide improved treatment of brain tumors.

2. Description of Related Art

There is an urgent need for novel therapeutics to treat brain tumors, especially astrocytomas grade IV (also known as glioblastomas multiforme). These tumors progress rapidly through healthy brain parenchyma and resist all current therapeutic approaches, making them one of the most devastating of all cancers. Patients diagnosed with astrocyomas grade IV typically die within a year. Even aggressive therapeutic interventions (i.e., combining surgery, radiotherapy and available chemotherapeutics) extend the life expectancy of these patients by only a few months. All drugs and adjuvants developed to kill astrocytomas (e.g., novel alkylating agents and monoclonal antibodies) have produced minimal therapeutic benefits, if any. Thus, a radically different therapeutic approach needs to be identified and implemented so that we can reliably treat these devastating tumors.

Because of the shortcomings of existing brain cancer treatments, there is a need in the art for improved therapies that provide meaningful therapeutic intervention against brain tumors. In recent years, a number of studies have suggested the existence of receptors activated by the cannabinoid-like compounds: the aminoalkylindoles (AAI). There is a need in the art to identify new compounds that selectively activate AAI receptors. AAI receptors may also be implicated in disease and to use such receptors, alone or as part of a panel of other receptors, to identify and profile the effects of potential therapeutic compounds capable of treating one or other of the many diseases and disorders mediated by AAI receptors.

SUMMARY

The disclosure provides improved methods and pharmaceutical compositions for treating brain tumors. Also provided are methods of screening for compounds that provide improved treatment of brain tumors.

In broad aspect, the disclosure provides methods of treating or inhibiting glioblastoma in a subject, the method comprising administering to the subject an effective amount of a compound of formula (I):

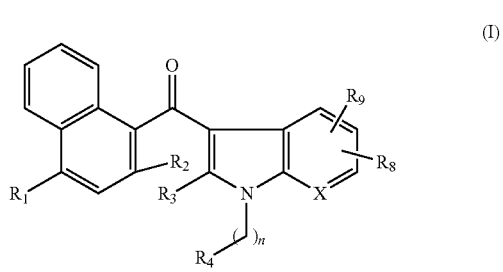

or pharmaceutically acceptable salts thereof, wherein
X is CH or N;
$R_1$, $R_2$, $R_3$ are each independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —ORhd 5, —$SR_S$, —C(O)$R_5$, —NHC(O)$R_5$, —C(O)O$R_5$, —OC(O)$R_5$, —$NR_6R_7$, —C(O)$NR_6R_7$, —$NHR_5$C(O)$NR_6R_7$, —$SO_2NR_6R_7$, alkylaryl, cycloalkyl, heterocyclyl, or heteroaryl, each being optionally substituted with one to four $R_{10}$;
$R_4$ is H, $C_1$-$C_6$ alkyl, aryl, $C_1$-$C_6$ alkylaryl, cycloalkyl, heterocyclyl, or heteroaryl, each being optionally substituted with one to four $R_{10}$, or
$R_4$ and $R_3$ taken together with the atoms to which they are attached form a 5-, 6-, or 7-membered heterocyclyl group optionally substituted with one to four $R_{10}$;
$R_5$, $R_6$, and $R_7$ are independently H, $C_1$-$C_6$ alkyl, $C_2$-$C_6$ alkenyl, $C_2$-$C_6$ alkynyl, $C_1$-$C_6$ alkoxy, halogen, hydroxyl, aryl, alkylaryl, cycloalkyl, heterocyclyl, or heteroaryl, each being optionally substituted with one to four $R_{10}$;
$R_8$ and $R_9$ are each independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ hydroxyalkyl, halogen, —$NO_2$, —CN, —ORhd 5, —$SR_S$, —C(O)$R_5$, —NHC(O)$R_5$, —C(O)O$R_5$, —OC(O)$R_5$, —$NR_6R_7$, —C(O)$NR_6R_7$, —$NHR_5$C(O) $NR_6R_7$, —$SO_2NR_6R_7$, alkylaryl, cycloalkyl, heterocyclyl, or heteroaryl, each being optionally substituted with one to four $R_{10}$,
or $R_4$ and $R_8$ taken together with the atoms to which they are attached form a 5-, 6-, or 7-membered cycloalkyl, heterocyclyl, aryl, or heteroaryl group, each being optionally substituted with one to four $R_{10}$;
$R_{10}$ is halogen, —CN, —OH, —$NO_2$, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkoxy, $C_1$-$C_6$ haloalkoxy, —$CO_2H$, —$CO_2$($C_1$-$C_6$ alkyl), —$SO_2$ ($C_1$-$C_6$ alkyl), —$CONH_2$, —CONH($C_1$-$C_6$ alkyl), —CON ($C_1$-$C_6$ alkyl)$_2$, —CON(H)OH, —NHCO($C_1$-$C_6$ alkyl), or —$NHCO_2$($C_1$-$C_6$ alkyl); and
n is an integer selected from the group consisting of 0, 1, 2, and 3.

In one aspect, the disclosure provides for methods of activating the GPR124 receptor comprising administering a compound formula (I).

In another aspect, the disclosure provides for a method of screening for therapeutic agents useful in the treatment of glioblastomas.

The disclosure also provides compounds of formula (II)

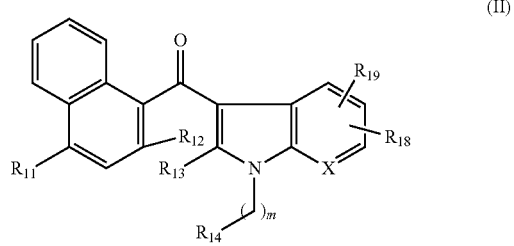

or pharmaceutically acceptable salts, wherein

X is CH or N;

$R_{11}$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —$OR_{15}$, —$SR_{15}$, —C(O)$R_{15}$, —NHC(O)$R_{15}$, —C(O)O$R_{15}$, —OC(O)$R_{15}$, —$NR_{16}R_{17}$, —C(O)$NR_{16}R_{17}$, —$NHR_{15}$C(O)$NR_{16}R_{17}$, —$SO_2NR_{16}R_{17}$, alkylaryl, cycloalkyl, heterocyclyl, or heteroaryl, each being optionally substituted with one to four $R_{20}$;

$R_{12}$ is H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —$OR_{15}$, —$SR_{15}$, —C(O)$R_{15}$, —NHC(O)$R_{15}$, —C(O)O$R_{15}$, —OC(O)$R_{15}$, —$NR_{16}R_{17}$, —C(O)$NR_{16}R_{17}$, —$NHR_{15}$C(O)$NR_{16}R_{17}$, —$SO_2NR_{16}R_{17}$, alkylaryl, cycloalkyl, heterocyclyl, or heteroaryl, each being optionally substituted with one to four $R_{20}$;

$R_{13}$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —ORhd is, —$SR_{15}$, —C(O)$R_{15}$, —NHC(O)$R_{15}$, —C(O)O$R_{15}$, —OC(O)$R_{15}$, —$NR_{16}R_{17}$, —C(O)$NR_{16}R_{17}$, —$NHR_{15}$C(O)$NR_{16}R_{17}$, —$SO_2NR_{16}R_{17}$, alkylaryl, cycloalkyl, heterocyclyl, or heteroaryl, each being optionally substituted with one to four $R_{20}$;

$R_{14}$ is H, aryl, cycloalkyl, heterocyclyl, or heteroaryl, each being optionally substituted with one to four $R_{20}$, or $R_{14}$ and $R_{13}$ taken together with the atoms to which they are attached form a 5-, 6-, or 7-membered heterocyclyl group optionally substituted with one to four $R_{20}$;

$R_{15}$, $R_{16}$, and $R_{17}$ are independently H, $C_1$-$C_6$ alkyl, $C_2$-$C_6$ alkenyl, $C_2$-$C_6$ alkynyl, $C_1$-$C_6$ alkoxy, halogen, hydroxyl, aryl, alkylaryl, cycloalkyl, heterocyclyl, or heteroaryl, each being optionally substituted with one to four $R_{20}$;

$R_{18}$ and $R_{19}$ are each independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ hydroxyalkyl, halogen, —$NO_2$, —CN, —$OR_{15}$, —$SR_{15}$, —C(O)$R_{15}$, —NHC(O)$R_{15}$, —C(O)O$R_{15}$, —OC(O)$R_{15}$, —$NR_{16}R_{17}$, —C(O)$NR_{16}R_{17}$, —$NHR_{15}$C(O)$NR_{16}R_{17}$, —$SO_2NR_{16}R_{17}$, alkylaryl, cycloalkyl, heterocyclyl, or heteroaryl, each being optionally substituted with one to four $R_{20}$, $R_{20}$ is halogen, —CN, —OH, —$NO_2$, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkoxy, $C_1$-$C_6$ haloalkoxy, —$CO_2$H, —$CO_2$($C_1$-$C_6$ alkyl), —$SO_2$($C_1$-$C_6$ alkyl), —$CONH_2$, —CONH($C_1$-$C_6$ alkyl), —CON($C_1$-$C_6$ alkyl)$_2$, —CON(H)OH, —NHCO($C_1$-$C_6$ alkyl), or —$NHCO_2$($C_1$-$C_6$ alkyl); and m is an integer 1 or 2.

The disclosure also provides a pharmaceutical composition comprising a therapeutically effective amount of a compound of formula (II), and one or more pharmaceutically acceptable diluents, preservatives, solubilizers, emulsifiers, adjuvants, excipients, or carriers.

The disclosure also provides methods of preparing compounds of the disclosure and the intermediates used in those methods.

The disclosure further provides a compound or pharmaceutical composition of the disclosure thereof in a kit with instructions for using the compound or composition.

The disclosure further provides compounds of the disclosure that may be administered alone or in combination with other drugs or therapies known to be effective to treat the disease to enhance overall effectiveness of therapy.

DETAILED DESCRIPTION

Figure 1:
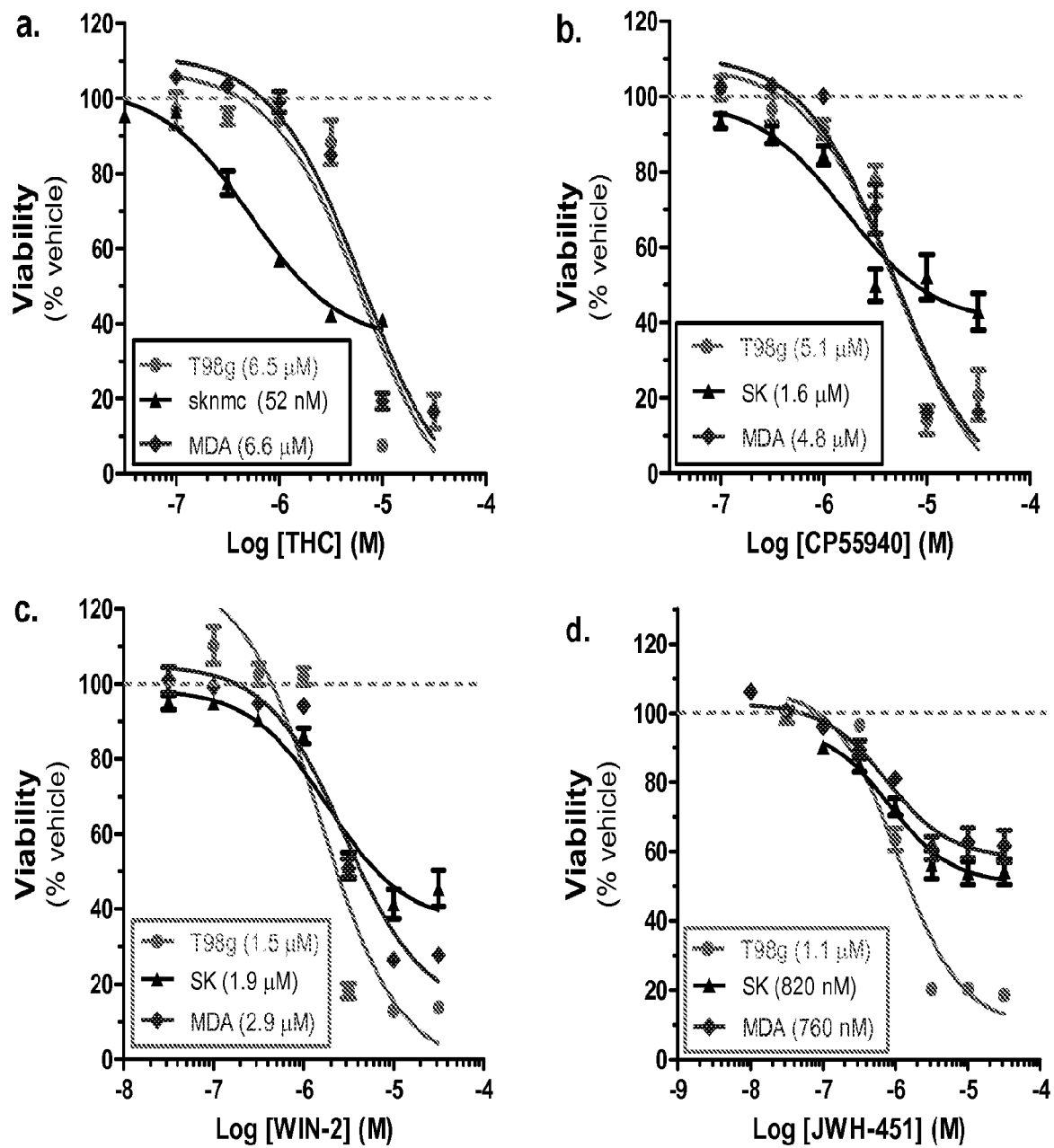
FIG. 1 illustrates toxic profile of a) THC, b) CP55940, c) WIN 55212-2 and d) JWH-451 in SK, MDA and T98g cells. Indicated are the EC50 of the respective toxic effect.

Briefly stated, the disclosure provides compounds, pharmaceutical compositions, and methods for treating brain tumors in a subject. Also provided are methods of screening for compounds and adjuvants that provide improved treatment of brain tumors.

Thus, in one aspect, the disclosure provides compounds of formula (II):

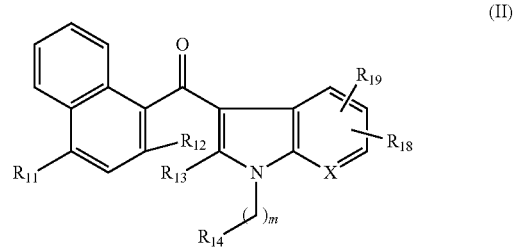

(II)

or pharmaceutically acceptable salts, wherein

X is CH or N;

$R_{11}$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —$OR_{15}$, —$SR_{15}$, —C(O)$R_{15}$, —NHC(O)$R_{15}$, —C(O)O$R_{15}$, —OC(O)$R_{15}$, —$NR_{16}R_{17}$, —C(O)$NR_{16}R_{17}$, —$NHR_{15}$C(O)$NR_{16}R_{17}$, —$SO_2NR_{16}R_{17}$, alkylaryl, cycloalkyl, heterocyclyl, or heteroaryl, each being optionally substituted with one to four $R_{20}$;

$R_{12}$ is H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —$OR_{15}$, —$SR_{15}$, —C(O)$R_{15}$, —NHC(O)$R_{15}$, —C(O)O$R_{15}$, —OC(O)$R_{15}$, —$NR_{16}R_{17}$, —$C(O)NR_{16}R_{17}$, —$NHR_{15}C(O)NR_{16}R_{17}$, —$SO_2NR_{16}R_{17}$, alkylaryl, cycloalkyl, heterocyclyl, or heteroaryl, each being optionally substituted with one to four $R_{20}$;

$R_{13}$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —$OR_{15}$, —$SR_{15}$, —$C(O)R_{15}$, —$NHC(O)R_{15}$, —$C(O)OR_{15}$, —$OC(O)R_{15}$, —$NR_{16}R_{17}$, —$C(O)NR_{16}R_{17}$, —$NHR_{15}C(O)NR_{16}R_{17}$, —$SO_2NR_{16}R_{17}$, alkylaryl, cycloalkyl, heterocyclyl, or heteroaryl, each being optionally substituted with one to four $R_{20}$;

$R_{14}$ is H, aryl, cycloalkyl, heterocyclyl, or heteroaryl, each being optionally substituted with one to four $R_{20}$, or $R_{14}$ and $R_{13}$ taken together with the atoms to which they are attached form a 5-, 6-, or 7-membered heterocyclyl group optionally substituted with one to four $R_{20}$;

$R_{15}$, $R_{16}$, and $R_{17}$ are independently H, $C_1$-$C_6$ alkyl, $C_2$-$C_6$ alkenyl, $C_2$-$C_6$ alkynyl, $C_1$-$C_6$ alkoxy, halogen, hydroxyl, aryl, alkylaryl, cycloalkyl, heterocyclyl, or heteroaryl, each being optionally substituted with one to four $R_{20}$;

$R_{18}$ and $R_{19}$ are each independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ hydroxyalkyl, halogen, —$NO_2$, —CN, —ORhd is, —$SR_{15}$, —$C(O)R_{15}$, —$NHC(O)R_{15}$, —$C(O)OR_{15}$, —$OC(O)R_{15}$, —$NR_{16}R_{17}$, —$C(O)NR_{16}R_{17}$, —$NHR_{15}C(O)NR_{16}R_{17}$, —$SO_2NR_{16}R_{17}$, alkylaryl, cycloalkyl, heterocyclyl, or heteroaryl, each being optionally substituted with one to four $R_{20}$, $R_{20}$ is halogen, —CN, —OH, —$NO_2$, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, —$CO_2H$, —$CO_2(C_1$-$C_6$ alkyl), —$SO_2(C_1$-$C_6$ alkyl), —$CONH_2$, —$CONH(C_1$-$C_6$ alkyl), —$CON(C_1$-$C_6$ alkyl$)_2$, —CON(H)OH, —$NHCO(C_1$-$C_6$ alkyl), or —$NHCO_2(C_1$-$C_6$ alkyl); and m is an integer 1 or 2.

In another aspect, the disclosure provides compounds of formula (II):

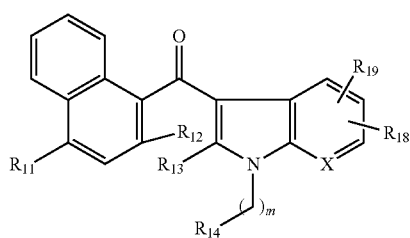

(II)

or pharmaceutically acceptable salts, wherein

X is CH or N;

$R_{11}$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —ORhd 15, —$SR_{15}$, —$C(O)R_{15}$, —$NHC(O)R_{15}$, —$C(O)OR_{15}$, —$OC(O)R_{15}$, —$NR_{16}R_{17}$, —$C(O)NR_{16}R_{17}$, —$NHR_{15}C(O)NR_{16}R_{17}$, —$SO_2NR_{16}R_{17}$, alkylaryl, cycloalkyl, heterocyclyl, or heteroaryl, each being optionally substituted with one to four $R_{20}$;

$R_{12}$ is H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —ORhd 15, —$SR_{15}$, —$C(O)R_{15}$, —$NHC(O)R_{15}$, —$C(O)OR_{15}$, —$OC(O)R_{15}$, —$NR_{16}R_{17}$, —$C(O)NR_{16}R_{17}$, —$NHR_{15}C(O)NR_{16}R_{17}$, —$SO_2NR_{16}R_{17}$, alkylaryl, cycloalkyl, heterocyclyl, or heteroaryl, each being optionally substituted with one to four $R_{20}$;

$R_{13}$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —ORhd 15, —$SR_{15}$, —$C(O)R_{15}$, —$NHC(O)R_{15}$, —$C(O)OR_{15}$, —$OC(O)Ris$, —$NR_{16}R_{17}$, —$C(O)NR_{16}R_{17}$, —$NHR_{15}C(O)NR_{16}R_{17}$, —$SO_2NR_{16}R_{17}$, alkylaryl, cycloalkyl, heterocyclyl, or heteroaryl, each being optionally substituted with one to four $R_{20}$;

$R_{14}$ is aryl, cycloalkyl, heterocyclyl, or heteroaryl, each being optionally substituted with one to four $R_{20}$, or $R_{14}$ and $R_{13}$ taken together with the atoms to which they are attached form a 5-, 6-, or 7-membered heterocyclyl group optionally substituted with one to four $R_{20}$;

$R_{15}$, $R_{16}$, and $R_{17}$ are independently H, $C_1$-$C_6$ alkyl, $C_2$-$C_6$ alkenyl, $C_2$-$C_6$ alkynyl, $C_1$-$C_6$ alkoxy, halogen, hydroxyl, aryl, alkylaryl, cycloalkyl, heterocyclyl, or heteroaryl, each being optionally substituted with one to four $R_{20}$;

$R_{18}$ and $R_{19}$ are each independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ hydroxyalkyl, halogen, —$NO_2$, —CN, —ORhd is, —$SR_{15}$, —$C(O)R_{15}$, —$NHC(O)R_{15}$, —$C(O)OR_{15}$, —$OC(O)R_{15}$, —$NR_{16}R_{17}$, —$C(O)NR_{16}R_{17}$, —$NHR_{15}C(O)NR_{16}R_{17}$, —$SO_2NR_{16}R_{17}$, alkylaryl, cycloalkyl, heterocyclyl, or heteroaryl, each being optionally substituted with one to four $R_{20}$, $R_{20}$ is halogen, —CN, —OH, —$NO_2$, —$NH_2$, —$NH(C_1$-$C_6$ alkyl), —$N(C_1$-$C_6$ alkyl$)_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, —$CO_2H$, —$CO_2(C_1$-$C_6$ alkyl), —$SO_2(C_1$-$C_6$ alkyl), —$CONH_2$, —$CONH(C_1$-$C_6$ alkyl), —$CON(C_1$-$C_6$ alkyl$)_2$, —CON(H)OH, —$NHCO(C_1$-$C_6$ alkyl), or —$NHCO_2(C_1$-$C_6$ alkyl); and m is an integer 1 or 2.

In yet another aspect, the disclosure provides compounds of formula (II):

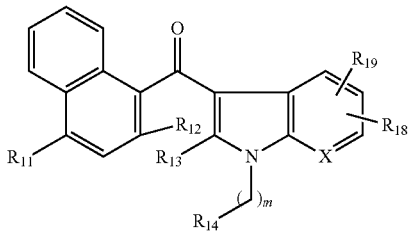

(II)

or pharmaceutically acceptable salts, wherein

X is CH or N;

$R_{11}$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —$OR_{15}$, —$SR_{15}$, —$C(O)R_{15}$, —$NHC(O)R_{15}$, —$C(O)OR_{15}$, —$OC(O)R_{15}$, —$NR_{16}R_{17}$, —$C(O)NR_{16}R_{17}$, —$NHR_{15}C(O)NR_{16}R_{17}$, —$SO_2NR_{16}R_{17}$, alkylaryl, cycloalkyl, heterocyclyl, or heteroaryl, each being optionally substituted with one to four $R_{20}$;

$R_{12}$ is H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —$OR_{15}$, —$SR_{15}$, —$C(O)R_{15}$, —$NHC(O)R_{15}$, —$C(O)OR_{15}$, —$OC(O)R_{15}$, —$NR_{16}R_{17}$, —$C(O)NR_{16}R_{17}$, —$NHR_{15}C(O)NR_{16}R_{17}$, —SO$_2$NR$_{16}$R$_{17}$, alkylaryl, cycloalkyl, heterocyclyl, or heteroaryl, each being optionally substituted with one to four R$_{20}$;

R$_{13}$ is C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ hydroxyalkyl, C$_1$-C$_6$ haloalkoxy, halogen, —NO$_2$, —CN, —ORhd is, —SR$_{15}$, —C(O)R$_{15}$, —NHC(O)R$_{15}$, —C(O)OR$_{15}$, —OC(O)R$_{15}$, —NR$_{16}$R$_{17}$, —C(O)NR$_{16}$R$_{17}$, —NHR$_{15}$C(O)NR$_{16}$R$_{17}$, —SO$_2$NR$_{16}$R$_{17}$, alkylaryl, cycloalkyl, heterocyclyl, or heteroaryl, each being optionally substituted with one to four R$_{20}$;

R$_{14}$ is aryl, cycloalkyl, heterocyclyl, or heteroaryl, each being optionally substituted with one to four R$_{20}$;

R$_{15}$, R$_{16}$, and R$_{17}$ are independently H, C$_1$-C$_6$ alkyl, C$_2$-C$_6$ alkenyl, C$_2$-C$_6$ alkynyl, C$_1$-C$_6$ alkoxy, halogen, hydroxyl, aryl, alkylaryl, cycloalkyl, heterocyclyl, or heteroaryl, each being optionally substituted with one to four R$_{20}$;

R$_{18}$ and R$_{19}$ are each independently H, C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ haloalkoxy, C$_1$-C$_6$ hydroxyalkyl, halogen, —NO$_2$, —CN, —OR$_{15}$, —SR$_{15}$, —C(O)R$_{15}$, —NHC(O)R$_{15}$, —C(O)OR$_{15}$, —OC(O)R$_{15}$, —NR$_{16}$R$_{17}$, —C(O)NR$_{16}$R$_{17}$, —NHR$_{15}$C(O)NR$_{16}$R$_{17}$, —SO$_2$NR$_{16}$R$_{17}$, alkylaryl, cycloalkyl, heterocyclyl, or heteroaryl, each being optionally substituted with one to four R$_{20}$, R$_{20}$ is halogen, —CN, —OH, —NO$_2$, —NH$_2$, —NH(C$_1$-C$_6$ alkyl), —N(C$_1$-C$_6$ alkyl)$_2$, C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ alkoxy, C$_1$-C$_6$ haloalkoxy, —CO$_2$H, —CO$_2$(C$_1$-C$_6$ alkyl), —SO$_2$(C$_1$-C$_6$ alkyl), —CONH$_2$, —CONH(C$_1$-C$_6$ alkyl), —CON(C$_1$-C$_6$ alkyl)$_2$, —CON(H)OH, —NHCO(C$_1$-C$_6$ alkyl), or —NHCO$_2$(C$_1$-C$_6$ alkyl); and m is an integer 1 or 2.

Thus, in another aspect, the disclosure provides compounds of formula (II):

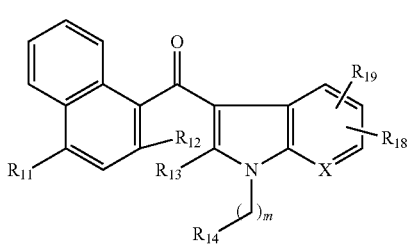

(II)

or pharmaceutically acceptable salts, wherein
X is CH or N;

R$_{11}$ is C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ hydroxyalkyl, C$_1$-C$_6$ haloalkoxy, halogen, —NO$_2$, —CN, —ORhd 15, —SR$_{15}$, —C(O)R$_{15}$, —NHC(O)R$_{15}$, —C(O)OR$_{15}$, —OC(O)R$_{15}$, —NR$_{16}$R$_{17}$, —C(O)NR$_{16}$R$_{17}$, —NHR$_{15}$C(O)NR$_{16}$R$_{17}$, —SO$_2$NR$_{16}$R$_{17}$, alkylaryl, cycloalkyl, heterocyclyl, or heteroaryl, each being optionally substituted with one to four R$_{20}$;

R$_{12}$ is H, C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ hydroxyalkyl, C$_1$-C$_6$ haloalkoxy, halogen, —NO$_2$, —CN, —ORhd is, —SR$_{15}$, —C(O)R$_{15}$, —NHC(O)R$_{15}$, —C(O)OR$_{15}$, —OC(O)R$_{15}$, —NR$_{16}$R$_{17}$, —C(O)NR$_{16}$R$_H$, —NHR$_{15}$C(O)NR$_{16}$R$_{17}$, —SO$_2$NR$_{16}$R$_{17}$, alkylaryl, cycloalkyl, heterocyclyl, or heteroaryl, each being optionally substituted with one to four R$_{20}$;

R$_{13}$ is C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ hydroxyalkyl, C$_1$-C$_6$ haloalkoxy, halogen, —NO$_2$, —CN, —ORhd 15, —SR$_{15}$, —C(O)R$_{15}$, —NHC(O)R$_{15}$, —C(O)OR$_{15}$, —OC(O)R$_{15}$, —NR$_{16}$R$_{17}$, —C(O)NR$_{16}$R$_H$, —NHR$_{15}$C(O)NR$_{16}$R$_{17}$, —SO$_2$NR$_{16}$R$_{17}$, alkylaryl, cycloalkyl, heterocyclyl, or heteroaryl, each being optionally substituted with one to four R$_{20}$;

R$_{14}$ is H;

R$_{15}$, R$_{16}$, and R$_{17}$ are independently H, C$_1$-C$_6$ alkyl, C$_2$-C$_6$ alkenyl, C$_2$-C$_6$ alkynyl, C$_1$-C$_6$ alkoxy, halogen, hydroxyl, aryl, alkylaryl, cycloalkyl, heterocyclyl, or heteroaryl, each being optionally substituted with one to four R$_{20}$;

R$_{18}$ and R$_{19}$ are each independently H, C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ haloalkoxy, C$_1$-C$_6$ hydroxyalkyl, halogen, —NO$_2$, —CN, —OR$_{15}$, —SR$_{15}$, —C(O)R$_{15}$, —NHC(O)R$_{15}$, —C(O)OR$_{15}$, —OC(O)R$_{15}$, —NR$_{16}$R$_{17}$, —C(O)NR$_{16}$R$_{17}$, —NHR$_{15}$C(O)NR$_{16}$R$_{17}$, —SO$_2$NR$_{16}$R$_{17}$, alkylaryl, cycloalkyl, heterocyclyl, or heteroaryl, each being optionally substituted with one to four R$_{20}$, R$_{20}$ is halogen, —CN, —OH, —NO$_2$, —NH$_2$, —NH(C$_1$-C$_6$ alkyl), —N(C$_1$-C$_6$ alkyl)$_2$, C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, C$_1$-C$_6$ alkoxy, C$_1$-C$_6$ haloalkoxy, —CO$_2$H, —CO$_2$(C$_1$-C$_6$ alkyl), —SO$_2$(C$_1$-C$_6$ alkyl), —CONH$_2$, —CONH(C$_1$-C$_6$ alkyl), —CON(C$_1$-C$_6$ alkyl)$_2$, —CON(H)OH, —NHCO(C$_1$-C$_6$ alkyl), or —NHCO$_2$(C$_1$-C$_6$ alkyl); and m is an integer 1 or 2.

In one embodiment, the disclosure as described above provides compounds wherein X of formula (II) is CH. In another embodiment, X of formula (II) is N.

In one embodiment, the disclosure as described above provides compounds wherein R$_H$ is C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ hydroxyalkyl, C$_1$-C$_6$ haloalkoxy, halogen, —NO$_2$, —CN, —OR$_{15}$, —SR$_{15}$, —C(O)R$_{15}$, —NHC(O)R$_{15}$, —C(O)OR$_{15}$, —NR$_{16}$R$_{17}$, —C(O)NR$_{16}$R$_H$, —SO$_2$NR$_{16}$R$_{17}$, or alkylaryl, each optionally substituted with one to four R$_{20}$. In another embodiment, R$_u$ 1 is C$_1$-C$_6$ alkyl, C$_1$-C$_6$ haloalkyl, C$_1$-C$_6$ alkoxy, C$_1$-C$_6$ hydroxyalkyl, C$_1$-C$_6$ haloalkoxy, halogen, —NO$_2$, —CN, —OR$_{15}$, —C(O)R$_{15}$, —C(O)OR$_{15}$, —NR$_{16}$R$_{17}$, or —C(O)NR$_{16}$R$_{17}$. In yet another embodiment, R$_{11}$ is C$_1$-C$_6$ alkyl, C$_1$-C$_6$ haloalkyl, C$_1$-C$_6$ alkoxy, C$_1$-C$_6$ haloalkoxy, halogen, —NO$_2$, —CN, —ORhd 15, —C(O)R$_{15}$, —C(O)OR$_{15}$, —NR$_{16}$R$_{17}$, or —C(O)NR$_{16}$R$_{17}$. In some embodiments, R$_{11}$ is C$_1$-C$_6$ alkyl, C$_1$-C$_6$ haloalkyl, C$_1$-C$_6$ alkoxy, halogen, —ORhd is, or —NR$_{16}$R$_{17}$.

In another embodiment, the disclosure as described above provides compounds wherein R$_H$ is C$_1$-C$_6$ alkyl or C$_1$-C$_6$ alkoxy. More specifically, R$_{11}$ is C$_1$-C$_4$ alkyl or C$_1$-C$_4$ alkoxy. Even more specifically, R$_{11}$ is methyl or methoxy. For example, R$_{11}$ is methyl.

In certain embodiments, the disclosure as described above provides compounds wherein R$_{12}$ is H or C$_1$-C$_6$ alkyl optionally substituted with R$_{20}$. In one embodiment, R$_{12}$ is H.

The disclosure as described above also provides compounds wherein R$_{13}$ is C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ hydroxyalkyl, C$_1$-C$_6$ haloalkoxy, halogen, —NO$_2$, —CN, —ORhd 15, —SR$_{15}$, —C(O)R$_{15}$, —NHC(O)R$_{15}$, —C(O)OR$_{15}$, —NR$_{16}$R$_{17}$, —C(O)NR$_{16}$R$_{17}$, —SO$_2$NR$_{16}$R$_{17}$, or alkylaryl, each optionally substituted with one to four R$_{20}$. In another embodiment, R$_{13}$ is C$_1$-C$_6$ alkyl, C$_1$-C$_6$ haloalkyl, C$_1$-C$_6$ alkoxy, C$_1$-C$_6$ hydroxyalkyl, C$_1$-C$_6$ haloalkoxy, halogen, —NO$_2$, —CN, —ORhd 15, —C(O)R$_{15}$, —C(O)OR$_{15}$, —NR$_{16}$R$_{17}$, or —C(O)NR$_{16}$R$_{17}$. In yet another embodiment, $R_{13}$ is $C_1$-$C_6$ alkyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —ORhd 15, —C(O)$R_{15}$, —C(O)O$R_{15}$, —N$R_{16}R_{17}$, or —C(O)N$R_{16}R_{17}$. In some embodiments, $R_{13}$ is $C_1$-$C_6$ alkyl, $C_1$-$C_6$ haloalkyl, $C_1$-$C_6$ alkoxy, halogen, —ORhd is, or —N$R_{16}R_{17}$.

In another embodiment, the disclosure as described above provides compounds wherein $R_{13}$ is $C_1$-$C_6$ alkyl. More specifically, $R_{13}$ is $C_1$-$C_4$ alkyl. Even more specifically, $R_{13}$ is methyl.

The disclosure as described above also provides compounds wherein $R_{13}$ and $R_{14}$ taken together with the atoms to which they are attached form a 5-, 6-, or 7-membered heterocyclyl group, each being optionally substituted with one to four $R_{20}$. In one embodiment, $R_{13}$ and $R_{14}$ taken together with the atoms to which they are attached form a 5-, or 6-membered heterocyclyl. In another embodiment, $R_{13}$ and $R_{14}$ taken together with the atoms to which they are attached form a 6-membered heterocyclyl (e.g., piperidinyl, piperazinyl, morpholinyl, etc.) In one embodiment, the heterocyclyl is piperidinyl.

In one embodiment, the disclosure as described above provides compounds wherein $R_{14}$ is H.

In another embodiment, the disclosure as described above provides compounds wherein $R_{14}$ is aryl, cycloalkyl, heterocyclyl, or heteroaryl, each being optionally substituted with one to four $R_{20}$. In yet another embodiment, $R_{14}$ is heterocyclyl or heteroaryl, each optionally substituted with $R_{20}$. In some embodiments, $R_{14}$ is heterocyclyl (e.g., piperidinyl, piperazinyl, morpholinyl, etc.) In one embodiment, $R_{14}$ is morpholinyl.

The disclosure as described above provides compounds wherein $R_{18}$ and $R_{19}$ are each independently H, $C_1$-$C_6$ alkyl, $C_1$-$C_6$ haloalkyl, $C_1$-$C_6$ alkoxy, $C_1$-$C_6$ haloalkoxy, $C_1$-$C_6$ hydroxyalkyl, halogen, —$NO_2$, —CN, —ORhd 15, —S$R_{15}$, —C(O)$R_{15}$, —C(O)O$R_{15}$, —N$R_6R_{17}$, —C(O)N$R_{16}R_{12}$, or —$SO_2NR_{16}R_{12}$, each being optionally substituted with one to four $R_{20}$. In one embodiment, $R_{18}$ and $R_{19}$ are each independently H, $C_1$-$C_6$ alkyl, $C_1$-$C_6$ haloalkyl, $C_1$-$C_6$ alkoxy, $C_1$-$C_6$ haloalkoxy, halogen, —$NO_2$, —CN, —ORhd is, or —N$R_{16}R_{12}$. In another embodiment, $R_{18}$ and $R_{19}$ are each independently H, $C_1$-$C_6$ alkyl, $C_1$-$C_6$ haloalkyl, $C_1$-$C_6$ alkoxy, $C_1$-$C_6$ haloalkoxy, halogen, or —OH.

The disclosure as described above also provides compounds $R_{18}$ and $R_{19}$ are each independently H, $C_1$-$C_6$ alkoxy, $C_1$-$C_6$ haloalkoxy, halogen, or —OH. In one embodiment, one of $R_{18}$ and $R_{19}$ is H, and the other is $C_1$-$C_6$ alkoxy, $C_1$-$C_6$ haloalkoxy, halogen, or —OH. In another embodiment, one of $R_{18}$ and $R_{19}$ is H, and the other is $C_1$-$C_6$ alkoxy or halogen. In yet another embodiment, one of $R_{18}$ and $R_{19}$ is H, and the other is halogen. In some embodiments, both $R_{18}$ and $R_{19}$ are H. In other embodiments, both $R_{18}$ and $R_{19}$ are halogen.

In certain specific embodiments, the disclosure as described above provides compounds wherein $R_{14}$ and $R_{18}$ taken together with the atoms to which they are attached form a 5-, 6-, or 7-membered cycloalkyl, heterocyclyl, aryl, or heteroaryl group, each being optionally substituted with one to four $R_{20}$. In one embodiment, $R_{14}$ and $R_{18}$ taken together with the atoms to which they are attached form a 6-membered heterocyclyl group, optionally substituted with $R_{20}$.

In certain embodiments, the disclosure provides compounds of formula (II) wherein $R_{14}$ is H. In other embodiments, $R_H$ is $C_1$-$C_6$ alkyl; $R_{12}$ is H, $R_{13}$ is $C_1$-$C_6$ alkyl; $R_{14}$ is H; and $R_{18}$ and $R_{19}$ are each independently H, $C_1$-$C_6$ alkyl, halogen, or —OH.

In other embodiments, the disclosure provides compounds of formula (II) wherein $R_{14}$ is heterocyclyl or heteroaryl, each optionally substituted with $R_{20}$. In some other embodiments, $R_H$ is $C_1$-$C_6$ alkyl; $R_{12}$ is H, $R_{13}$ is $C_1$-$C_6$ alkyl; $R_{14}$ is heterocyclyl or heteroaryl, each optionally substituted with $R_{20}$; and $R_{18}$ and $R_{19}$ are each independently H, $C_1$-$C_6$ alkyl, halogen, or —OH.

In other embodiments, the disclosure provides compounds of formula (II) wherein $R_H$ is $C_1$-$C_6$ alkyl; $R_{12}$ is H; $R_{13}$ and $R_{14}$ taken together with the atoms to which they are attached form a 5-, or 6-membered heterocyclyl; and $R_{18}$ and $R_{19}$ are each independently H, $C_1$-$C_6$ alkyl, halogen, or —OH.

In one embodiment, the disclosure provides compounds of formula (II), which is:

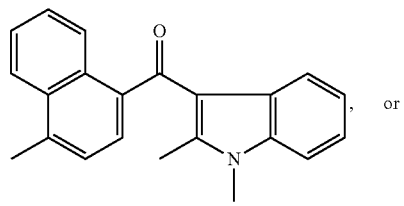, or

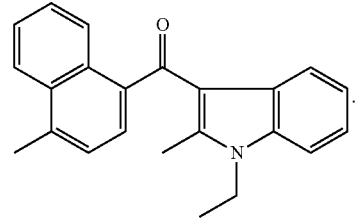 [SMILES: Cc1ccc(C(=O)c2c3n(c4ccccc24)CCCC3)c2ccccc12].

In one embodiment, the disclosure provides compounds of formula (II), which is:

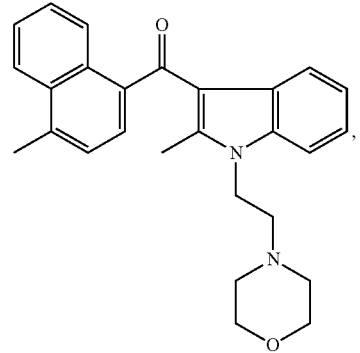,

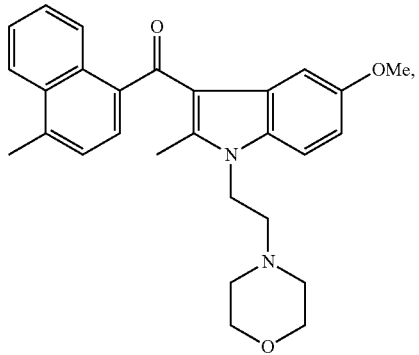

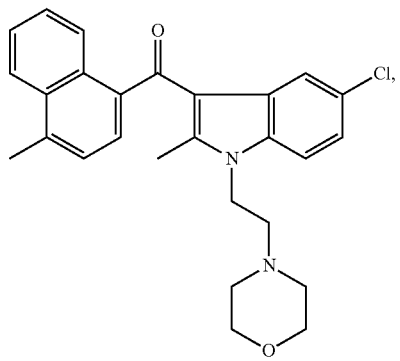

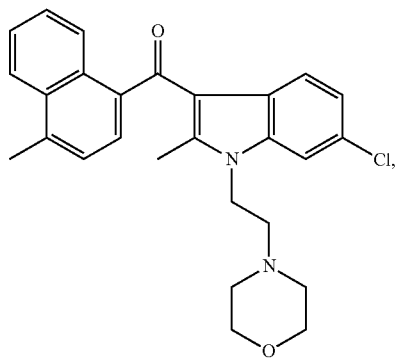

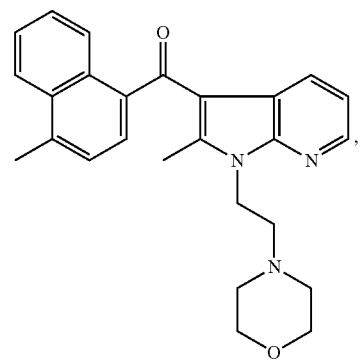

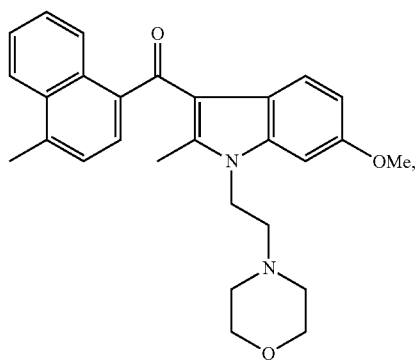

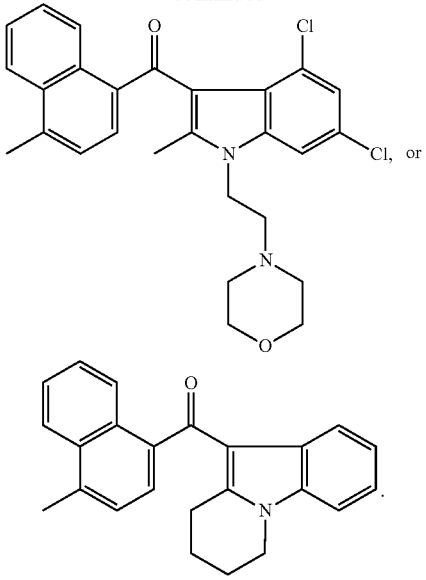

Pharmaceutical Formulations and Modes of Administration

In various aspects, the disclosure provides a pharmaceutical composition comprising a therapeutically effective amount of a compound of formula (II), and one or more pharmaceutically acceptable diluents, preservatives, solubilizers, emulsifiers, adjuvants, excipients, or carriers.

In certain aspects, the disclosure provides for a pharmaceutical composition comprising the compounds of the disclosure together with one or more pharmaceutically acceptable excipients or vehicles, and optionally other therapeutic and/or prophylactic ingredients. Such excipients include liquids such as water, saline, glycerol, polyethyleneglycol, hyaluronic acid, ethanol, and the like.

The term "pharmaceutically acceptable vehicle" refers to a diluent, adjuvant, excipient or carrier with which a compound of the disclosure is administered. The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. For example, an "effective amount" for therapeutic uses is the amount of the composition comprising one or more polyene macrolide compounds disclosed herein required to treat diseases caused by fungal infections to provide a clinically significant decrease in infections. An appropriate "effective" amount in any individual case can be determined by one of ordinary skill in the art using routine experimentation.

"Pharmaceutically acceptable carriers" for therapeutic use are well known in the pharmaceutical art, and are described, for example, in *Remington's Pharmaceutical Sciences*, 18th Edition (Easton, Pa.: Mack Publishing Company, 1990). For example, sterile saline and phosphate-buffered saline at physiological pH can be used. Preservatives, stabilizers, dyes and even flavoring agents can be provided in the pharmaceutical composition. For example, sodium benzoate, sorbic acid and esters of p-hydroxybenzoic acid can be added as preservatives. Id. at 1449. In addition, antioxidants and suspending agents can be used. Id.

Suitable excipients for non-liquid formulations are also known to those of skill in the art. A thorough discussion of pharmaceutically acceptable excipients and salts is available in Remington's Pharmaceutical Sciences, 18th Edition (Easton, Pa.: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

The disclosure includes a pharmaceutical composition comprising a compound of the disclosure including isomers, racemic or non-racemic mixtures of isomers, or pharmaceutically acceptable salts or solvates thereof together with one or more pharmaceutically acceptable carriers, and optionally other therapeutic and/or prophylactic ingredients.

In general, the compounds of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the disclosure for a given disease.

Thus, the compounds of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compounds of the disclosure can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Thus, for example, capsules can be prepared by conventional procedures so that the dosage unit is 100 mg of the compounds of the disclosure, 100 mg of cellulose and 10 mg of magnesium stearate. A large number of unit capsules can also prepared by filling standard two-piece hard gelatin capsules each with 100 mg of powdered active ingredient, 150 mg of lactose, 50 mg of cellulose, and 10 mg magnesium stearate. Or, tablets can be prepared by conventional procedures so that the dosage unit is 100 mg of the compounds of the disclosure, 150 mg of lactose, 50 mg of cellulose and 10 mg of magnesium stearate. A large number of tablets can also be prepared by conventional procedures such that the dosage unit was 100 mg of the compounds of the disclosure, and other ingredients can be 0.2 mg of colloidal silicon dioxide, 5 mg of magnesium stearate, 250 mg of microcrystalline cellulose, 10 mg of starch and 100 mg of lactose. Appropriate coatings can be applied to increase palatability or delay absorption.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as an continuous infusion system. A formulation provided by the disclosure can be administered using a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

The formulations can optionally contain an isotonicity agent. The formulations preferably contain an isotonicity agent, and glycerin is the most preferred isotonicity agent. The concentration of glycerin, when it is used, is in the range known in the art, such as, for example, about 1 mg/mL to about 20 mg/mL.

The pH of the parenteral formulations can be controlled by a buffering agent, such as phosphate, acetate, TRIS or L-arginine. The concentration of the buffering agent is preferably adequate to provide buffering of the pH during storage to maintain the pH at a target pH±0.2 pH unit. The preferred pH is between about 7 and about 8 when measured at room temperature.

Other additives, such as a pharmaceutically acceptable solubilizers like Tween 20® (polyoxyethylene (20) sorbitan monolaurate), Tween 40® (polyoxyethylene (20) sorbitan monopalmitate), Tween 80® (polyoxyethylene (20) sorbitan monooleate), Pluronic F68® (polyoxyethylene polyoxypropylene block copolymers), and PEG (polyethylene glycol) can optionally be added to the formulation, and can be useful if the formulations will contact plastic materials. In addition, the parenteral formulations can contain various antibacterial and antifungal agents, for example, parabens, chlorobutanol, phenol, sorbic acid, thimerosal, and the like.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmucosal delivery system as known to those skilled in the art. The compounds of the disclosure can also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

The compounds of the disclosure can be formulated for aerosol administration, particularly to the respiratory tract and including intranasal administration. The compound will generally have a small particle size for example of the order of 5 microns or less. Such a particle size can be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve. Alternatively the active ingredients can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. For purposes of the disclosure, generally a therapeutic amount will be in the range of about 0.01 mg/kg to about 250 mg/kg body weight, more preferably about 0.1 mg/kg to about 10 mg/kg, in at least one dose. In larger mammals the indicated daily dosage can be from about 1 mg to 300 mg, one or more times per day, more preferably in the range of about 10 mg to 200 mg. The subject can be administered as many doses as is required to reduce and/or alleviate the signs, symptoms, or causes of the disorder in question, or bring about any other desired alteration of a biological system. When desired, formulations can be pre pared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Methods of Treating of Glioblastoma

WIN 55212-2 (WIN-2) was reported to bind with nanomolar affinity to a protein expressed by NG108-15 cells. CP55, 940 (CP), a high-affinity agonist at $CB_1$ and $CB_2$ receptors, did not compete for WIN-2 binding in these cells. WIN-2 was reported to increase $[^{35}S]$-GTPγS binding in homogenates prepared from $CB_1$-/- mice cerebellum, a response insensitive to the $CB_2$ antagonist SR144528. WIN-2 was also reported to inhibit excitatory transmission in hippocampal slices prepared from $CB_1$-/- mice, and subsequently showed that this response is blocked by the TRPV1 antagonist capsazepine. Together, these findings suggest that a receptor activated by the aminoalkylindole compound WIN-2 exists and that it is a G protein-coupled receptor (GPCR).

G protein-coupled receptors (GPCRs) constitute a family of proteins sharing a common structural organization characterized by an extracellular N-terminal end, seven hydrophobic alpha helices putatively constituting transmembrane domains, and an intracellular C-terminal domain. GPCRs bind a wide variety of ligands that trigger intracellular signals through the activation of transducing G proteins. More than 300 GPCRs have been cloned, and it is generally assumed that well over 1,000 of such receptors exist. Roughly 50-60% of all clinically relevant drugs act by modulating the functions of various GPCRs.

Activation of $CB_1$ and $CB_2$ receptors kill astrocytomas. In the mid-1990s, $CB_1$ receptors were reported to be present in various human glioma cell lines, as well as explants of human tumors with various degrees of malignancy. Accordingly, agonists at $CB_1$ receptors active the ERK kinase pathway and transcription factor krox-24 in human glioma cell lines in culture, responses antagonized by the $CB_1$ receptor antagonist rimonabant applied a nanomolar concentrations. Shortly after these publications, cannabinoids were hypothesized to serve as powerful anti-tumoral agents in the treatment of astrocytomas.

As the prototypical AAI compound, WIN-2, was originally synthesized as an anti-inflammatory and analgesic agent. Its serendipitous pharmacological targeting of $CB_1/CB_2$ has served as a highly efficacious tool to study cannabinoid signaling, and more interestingly to our study, has revealed non-$CB_1/CB_2$-mediated effects. The disclosure shows that mouse and human astrocytomas cell line express GPR124, a AAI receptor; and that agonists at GPR124 receptor selectively kill tumor cells without harming healthy cells.

The disclosure also provides methods of treating or inhibiting glioblastoma in a subject, the method comprising administering to the subject an effective amount of a compound of formula (II), wherein $R_{11}$-$R_{14}$, $R_{18}$, $R_{19}$, X and m are as defined above.

The disclosure provides methods of treating or inhibiting glioblastoma in a subject, the method comprising administer ing to the subject an effective amount of a compound of formula (I):

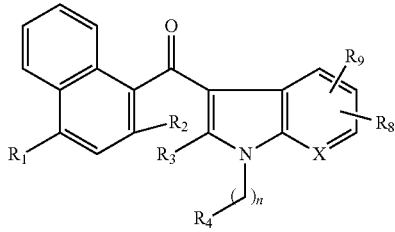

or pharmaceutically acceptable salts thereof, wherein
X is CH or N;
$R_1$, $R_2$, $R_3$ are each independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —ORhd 5, —$SR_5$, —C(O)$R_5$, —NHC(O)$R_5$, —C(O)O$R_5$, —OC(O)$R_5$, —$NR_6R_7$, —C(O)$NR_6R_7$, —$NHR_5$C(O)$NR_6R_7$, —$SO_2NR_6R_2$, alkylaryl, cycloalkyl, heterocyclyl, or heteroaryl, each being optionally substituted with one to four $R_{10}$;
$R_4$ is H, $C_1$-$C_6$ alkyl, aryl, $C_1$-$C_6$ alkylaryl, cycloalkyl, heterocyclyl, or heteroaryl, each being optionally substituted with one to four $R_{10}$, or
$R_4$ and $R_3$ taken together with the atoms to which they are attached form a 5-, 6-, or 7-membered heterocyclyl group optionally substituted with one to four $R_{10}$;
$R_5$, $R_6$, and $R_7$ are independently H, $C_1$-$C_6$ alkyl, $C_2$-$C_6$ alkenyl, $C_2$-$C_6$ alkynyl, $C_1$-$C_6$ alkoxy, halogen, hydroxyl, aryl, alkylaryl, cycloalkyl, heterocyclyl, or heteroaryl, each being optionally substituted with one to four $R_{10}$;
$R_8$ and $R_9$ are each independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ hydroxyalkyl, halogen, —$NO_2$, —CN, —ORhd 5, —$SR_S$, —C(O)$R_5$, —NHC(O)$R_5$, —C(O)O$R_5$, —OC(O)$R_5$, —$NR_6R_7$, —C(O)$NR_6R_7$, —$NHR_5$C(O)$NR_6R_7$, —$SO_2NR_6R_7$, alkylaryl, cycloalkyl, heterocyclyl, or heteroaryl, each being optionally substituted with one to four $R_{10}$,
or $R_4$ and $R_8$ taken together with the atoms to which they are attached form a 5-, 6-, or 7-membered cycloalkyl, heterocyclyl, aryl, or heteroaryl group, each being optionally substituted with one to four $R_{10}$;
$R_{10}$ is halogen, —CN, —OH, —$NO_2$, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkoxy, $C_1$-$C_6$ haloalkoxy, —$CO_2H$, —$CO_2$($C_1$-$C_6$ alkyl), —$SO_2$($C_1$-$C_6$ alkyl), —$CONH_2$, —CONH($C_1$-$C_6$ alkyl), —CON($C_1$-$C_6$ alkyl)$_2$, —CON(H)OH, —NHCO($C_1$-$C_6$ alkyl), or —$NHCO_2$($C_1$-$C_6$ alkyl); and
n is an integer selected from the group consisting of 0, 1, 2, and 3.

In one embodiment, the disclosure provides methods wherein X of formula (I) is CH. In another embodiment, X of formula (I) is N.

In one embodiment, the disclosure as described above provides methods wherein $R_1$ is H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —ORhd 5, —$SR_S$, —C(O)$R_5$, —NHC(O)$R_5$, —C(O)O$R_5$, —$NR_6R_7$, —C(O)$NR_6R_7$, —$SO_2NR_6R_7$, or alkylaryl, each optionally substituted with one to four $R_{10}$. In another embodiment, $R_1$ is H, $C_1$-$C_6$ alkyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —ORhd 5, —C(O)$R_5$, —C(O)O$R_5$, —$NR_6R_7$, or —C(O)$NR_6R_7$. In yet another embodiment, $R_1$ is $C_1$-$C_6$ alkyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —ORhd 5, —C(O)$R_5$, —C(O)O$R_5$, —$NR_6R_7$, or —C(O)$NR_6R_7$. In some embodiments, $R_1$ is $C_1$-$C_6$ alkyl, $C_1$-$C_6$ haloalkyl, $C_1$-$C_6$ alkoxy, halogen, —ORhd 5, or —$NR_6R_7$.

In another embodiment, the disclosure as described above provides methods wherein $R_1$ is $C_1$-$C_6$ alkyl or $C_1$-$C_6$ alkoxy. More specifically, $R_1$ is $C_1$-$C_4$ alkyl or $C_1$-$C_4$ alkoxy. Even more specifically, $R_1$ is methyl or methoxy. For example, $R_1$ is methyl.

In certain embodiments, the disclosure as described above provides methods wherein $R_2$ is H or $C_1$-$C_6$ alkyl optionally substituted with $R_{10}$. In one embodiment, $R_2$ is H.

The disclosure as described above also provides methods wherein $R_3$ is H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —ORhd 5, —$SR_S$, —C(O)$R_5$, —NHC(O)$R_5$, —C(O)O$R_5$, —$NR_6R_7$, —C(O)$NR_6R_7$, —$SO_2NR_6R_7$, or alkylaryl, each optionally substituted with one to four $R_{10}$. In another embodiment, $R_3$ is H, $C_1$-$C_6$ alkyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —ORhd 5, —C(O)$R_5$, —C(O)O$R_5$, —$NR_6R_7$, or —C(O)$NR_6R_7$. In yet another embodiment, $R_3$ is $C_1$-$C_6$ alkyl, $C_1$-$C_6$ haloalkyl, $C_1$-$C_6$ alkoxy, $C_1$-$C_6$ hydroxyalkyl, $C_1$-$C_6$ haloalkoxy, halogen, —$NO_2$, —CN, —ORhd 5, —C(O)$R_5$, —C(O)O$R_5$, —$NR_6R_7$, or —C(O)$NR_6R_7$. In some embodiments, $R_3$ is $C_1$-$C_6$ alkyl, $C_1$-$C_6$ haloalkyl, $C_1$-$C_6$ alkoxy, halogen, —ORhd 5, or —$NR_6R_7$.

In another embodiment, the disclosure as described above provides methods wherein $R_3$ is $C_1$-$C_6$ alkyl. More specifically, $R_3$ is $C_1$-$C_4$ alkyl. Even more specifically, $R_3$ is methyl.

The disclosure as described above also provides methods wherein $R_3$ and $R_4$ taken together with the atoms to which they are attached form a 5-, 6-, or 7-membered heterocyclyl group, each being optionally substituted with one to four $R_{10}$. In one embodiment, $R_3$ and $R_4$ taken together with the atoms to which they are attached form a 5-, or 6-membered heterocyclyl. In another embodiment, $R_3$ and $R_4$ taken together with the atoms to which they are attached form a 6-membered heterocyclyl (e.g., piperidinyl, piperazinyl, morpholinyl, etc.) In one embodiment, the heterocyclyl is piperidinyl.

In one embodiment, the disclosure as described above provides methods wherein $R_4$ is H or $C_1$-$C_6$ alkyl. In another embodiment, $R_4$ is H.

In another embodiment, the disclosure as described above provides methods wherein $R_4$ is aryl, cycloalkyl, heterocyclyl, or heteroaryl, each being optionally substituted with one to four $R_{10}$. In yet another embodiment, $R_4$ is heterocyclyl or heteroaryl, each optionally substituted with $R_{10}$. In some embodiments, $R_4$ is heterocyclyl (e.g., piperidinyl, piperazinyl, morpholinyl, etc.) In one embodiment, $R_4$ is morpholinyl.

The disclosure as described above provides compounds wherein $R_8$ and $R_9$ are each independently H, $C_1$-$C_6$ alkyl, $C_1$-$C_6$ haloalkyl, $C_1$-$C_6$ alkoxy, $C_1$-$C_6$ haloalkoxy, $C_1$-$C_6$ hydroxyalkyl, halogen, —$NO_2$, —CN, —ORhd 5, —$SR_S$, —C(O)$R_5$, —C(O)O$R_5$, —$NR_6R_7$, —C(O)$NR_6R_7$, or —$SO_2NR_6R_7$, each being optionally substituted with one to four $R_{10}$. In one embodiment, $R_8$ and $R_9$ are each independently H, $C_1$-$C_6$ alkyl, $C_1$-$C_6$ haloalkyl, —OH, $C_1$-$C_6$ alkoxy, $C_1$-$C_6$ haloalkoxy, halogen, —$NO_2$, —CN, —ORhd 5, or —$NR_6R_7$. In another embodiment, $R_8$ and $R_9$ are each independently H, $C_1$-$C_6$ alkyl, $C_1$-$C_6$ haloalkyl, —OH, $C_1$-$C_6$ alkoxy, $C_1$-$C_6$ haloalkoxy, or halogen.

The disclosure as described above also provides compounds $R_8$ and $R_9$ are each independently H, —OH, $C_1$-$C_6$ alkoxy, $C_1$-$C_6$ haloalkoxy, or halogen. In one embodiment, one of $R_8$ and $R_9$ is H, and the other is —OH, $C_1$-$C_6$ alkyl, $C_1$-$C_6$ haloalkoxy, or halogen. In another embodiment, one of $R_8$ and $R_9$ is H, and the other is $C_1$-$C_6$ alkoxy or halogen. In yet another embodiment, one of $R_8$ and $R_9$ is H, and the other is halogen. In some embodiments, both $R_8$ and $R_9$ are H. In other embodiments, both $R_8$ and $R_9$ are halogen.

In certain specific embodiments, the disclosure as described above provides methods wherein $R_4$ and $R_8$ taken together with the atoms to which they are attached form a 5-, 6-, or 7-membered cycloalkyl, heterocyclyl, aryl, or heteroaryl group, each being optionally substituted with one to four $R_{10}$. In one embodiment, $R_4$ and $R_8$ taken together with the atoms to which they are attached form a 6-membered heterocyclyl group, optionally substituted with $R_{10}$.

In certain specific embodiments, the disclosure as described above provides methods wherein $R_1$ is H or $C_1$-$C_6$ alkyl; $R_3$ is H or $C_1$-$C_6$ alkyl; n is 0; $R_4$ is $C_1$-$C_6$ alkyl; and $R_8$ and $R_9$ are each independently H, $C_1$-$C_6$ alkyl, halogen, or —OH.

In certain embodiments, the compounds of the methods of disclosure have the following structures:

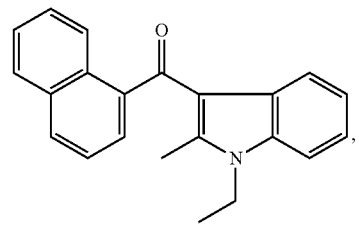

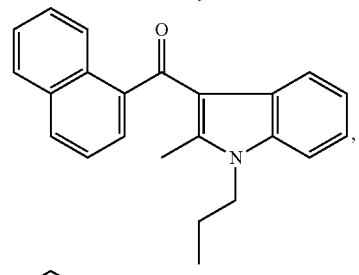

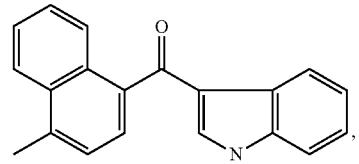

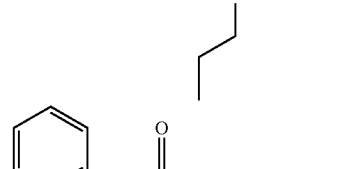

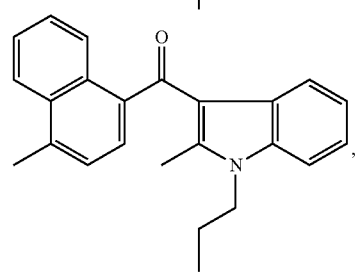

-continued

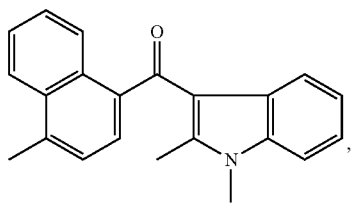

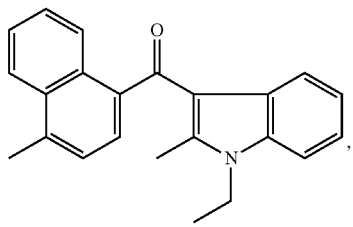

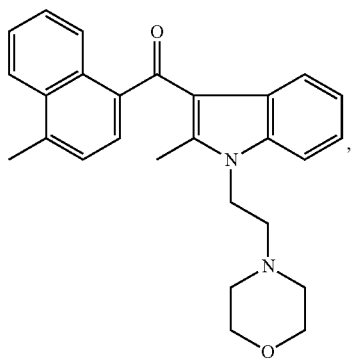

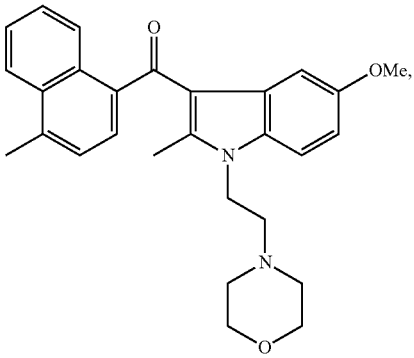

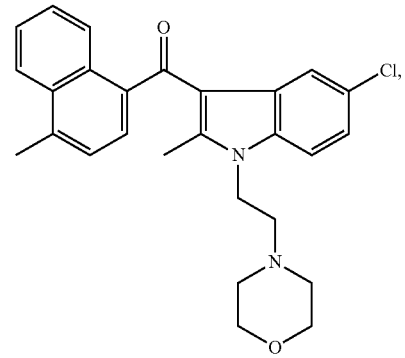

-continued

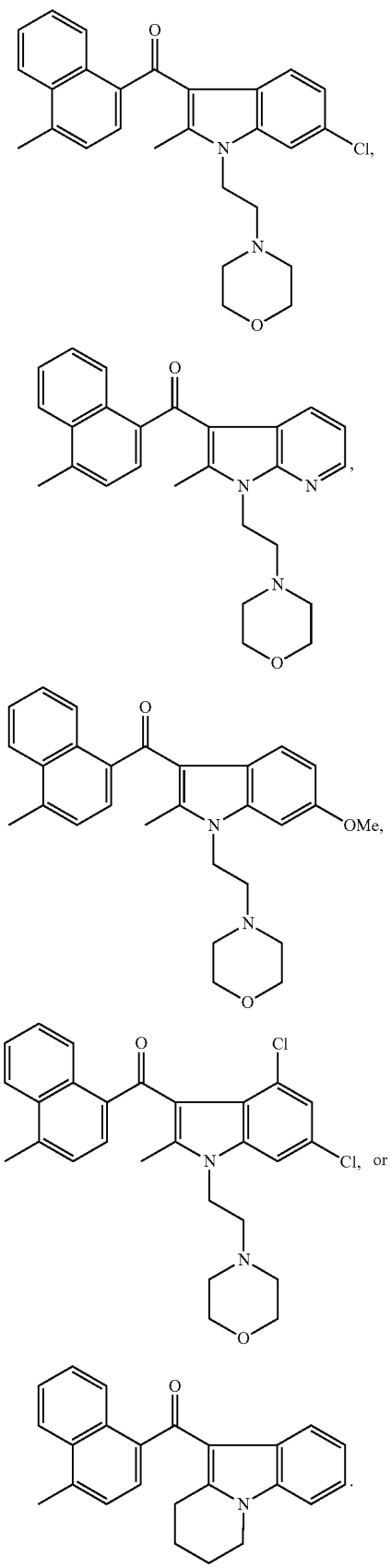

In another aspect, the disclosure provides for methods of activating the GPR124 receptor comprising administering a compound of formula (I) or (II) as defined above.

In various embodiments, the compounds of the disclosure bind to GPR124. In further embodiments, the compounds of the disclosure bind to no more than one of the CB1 or $CB_2$ cannabinoid receptors. In some embodiments, the compounds of the disclosure do not bind to the $CB_1$ or $CB_2$ cannabinoid receptors. In certain embodiments, the disclosure provides methods where astrocytomas are killed.

GPR124 was initially identified in endothelial cells derived from blood vessels growing in colorectal tumors. No compound acting through this receptor has been reported yet and its signal transduction mechanism is only starting to be delineated. Genetic approaches aimed at deleting or over-expressing GPR124 in selective cell populations show that this receptor plays a crucial role in the development of vasculature and the migration of endothelial cells. While the expression pattern of GPR124 in healthy human brain and in human GBMs still needs to be determined, the mouse brain atlas of the Allen Institute indicates that GPR124 is expressed at low level in healthy mouse brain.

In one embodiment, the compounds of the disclosure as defined above selectively bind to GPR124. In another embodiment, the compounds of the disclosure as defined above activate no more than one of the $CB_1$ or $CB_2$ cannabinoid receptors. In yet another embodiment, the compounds of the disclosure as defined above do not activate the $CB_1$ or $CB_2$ cannabinoid receptors.

The disclosure also provides methods of treating glioblastomas in a subject comprising activating the GPR124 receptor in the brain of the subject, comprising administering one or more of compounds of the disclosure as described above. In one embodiment, astrocytomas are killed. In additional embodiment, the $CB_1$ or $CB_2$ cannabinoid receptors are not activated by the treatment.

The disclosure further provides methods of enhancing GPR124 activity in a subject comprising administering an agonist of GPR124 in the brain of the subject. In further embodiment, the $CB_1$ or $CB_2$ cannabinoid receptors are not activated by the agonist. In one embodiment, the agonist is the compound of the disclosure as described above.

Screening Methods

In one aspect, the disclosure provides methods of screening for therapeutic agents useful in the treatment of glioblastomas in a subject, comprising the steps of:
contacting a test compound with a GPR124 polypeptide or a fragment thereof;
measuring a signal correlated with binding of the test compound to the GPR124 polypeptide;
contacting the test compound with the $CB_1$ cannabinoid receptor;
measuring a signal correlated with binding of the test compound to the $CB_1$ cannabinoid receptor;
contacting the test compound with the $CB_2$ cannabinoid receptor;
measuring a signal correlated with binding of the test compound to the $CB_2$ cannabinoid receptor; and
determining whether the test compound binds to the GPR124 polypeptide, $CB_1$ cannabinoid receptor, and $CB_2$ cannabinoid receptor; and
selecting a positive test compound that binds to the GPR124 polypeptide but not to one of the $CB_1$ or $CB_2$ cannabinoid receptors.

In one embodiment, the test compound is an agonist of GPR124. In further aspects, the test compound is an antagonist of GPR124. In another embodiment, the test compound is the compound of disclosure as described above.

In one embodiment, the disclosure provides methods of screening for therapeutic agents further comprising:

contacting a second test agent with a GPR124 polypeptide or a fragment thereof, wherein the GPR124 is bound to the positive test compound;

measuring a signal correlated with binding of the positive test compound to the GPR124 polypeptide;

selecting a second test compound that modulates the activity of the positive test compound at the GPR124 polypeptide.

In one embodiment, the step of contacting is in or at the surface of a cell. In other embodiment, the step of contacting is in a cell-free system.

In certain embodiments, the polypeptide is coupled to a detectable label. In other embodiments, the test compound is coupled to a detectable label. In another embodiment, the test compound displaces a ligand which is first bound to the polypeptide.

In one embodiment, the test compound is an agonist of GPR124. In further aspects, the test compound is an antagonist of GPR124. In another embodiment, the test compound is the compound of the disclosure as described above.

Kits

In other aspects, the disclosure provides for kits that can be used to perform the methods described herein. In various aspects, the kits comprise the compounds of the disclosure in one or more containers. In some aspects, the kits contain all of the components necessary and/or sufficient to administer the compounds of the disclosure to a subject, including instructions for administering the compounds. In some aspects, the kits contain all of the components necessary and/or sufficient to perform a the assays of the screening methods of the disclosure, including all controls, directions for performing assays, and any necessary software for analysis and presentation of results. In certain aspects, the disclosure provides for a compartment kit in which reagents are contained in separate containers. Such containers allow one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the soluble receptor used in the methods, containers which contain wash reagents (such as phosphate buffered saline, Tris-buffers, and the like), and containers which contain the reagents used to detect signals corresponding to binding of the CB 1 and CB2 receptors and the GPR124 receptor. One skilled in the art will readily recognize that the presently disclosed compounds can be readily incorporated into one of the established kit formats which are well known in the art.

In one embodiment, the disclosure provides for a kit comprising a compound of formula (I) as described above. In another embodiment, the disclosure provides for a kit comprising a compound of formula (II) as described above.

Other Therapeutic Methods

The disclosure also provides embodiments related to the interaction between AAIs compounds and other ligands and the AAI receptors. According to the disclosure, methods for the identification of compounds that modulate the binding of AAIs and other ligands to AAI receptors are provided. These methods are used to identify compounds that modulate AAI compounds and other ligand activation of AAI receptors, identify compounds that are agonists, antagonists, allosteric modulators, or inverse agonists of AAI receptors, and identify compounds that selectively modulate AAI receptors, rather than other receptors, such as CB1 or CB2. Assays of the disclosure can also be used to identify compounds having activity at any combination of CB1, CB2 and AAI receptors.

Modulation of the AAI binding site activity by endogenous, natural or synthetic agonists, antagonists or inverse agonists may be useful for the treatment (therapeutic or prophylactic) of a number of diseases $_w$here cannabinoid-like ligands play a key role or have a beneficial effect, $i_n$ particular but not limited to tissues where AAI binding site is expressed and where AAI are implicated to $h_a$ve a significant disease modifying effect, such as the prefrontal cortex, substantia nigra and nucleus basalis of Meynert in CNS and cognition disorders, ego schizophrenia, Alzheimer's disease and dementia, or the caudate and putamen in Parkinson's disease, depression, multiple sclerosis, and other pathologies associated with neuroinflammation (e.g., amyotrophic lateral sclerosis (ALS), Huntington's disease, Fronto temporal dementia, parkinsonism linked to chromosome 17 and prion diseases such as Kuru, Creutzfeld-Jacob disease, scrapie and bovine spongiform encephalitis, and the like). Thus, the disclosure provides method of treatment of a cognition disorders, schizophrenia, Alzheimer's disease and dementia, Parkinson's disease, depression, multiple sclerosis, amyotrophic lateral sclerosis (ALS), Huntington's disease, Fronto temporal dementia, parkinsonism linked to chromosome 17, and prion diseases (such as Kuru, Creutzfeld-Jacob disease, scrapie and bovine spongiform encephalitis) comprising administering to the subject an effective amount of a compound of formula (I) or formula (II) as described above.

Definitions

Any terms not directly defined herein shall be understood to have the meanings commonly associated with them as understood within the art of the disclosure. Certain terms are discussed herein to provide additional guidance to the practitioner in describing the compositions, devices, methods, and the like, of embodiments of the disclosure, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the embodiments of the disclosure herein.

It must be noted that, as used in the specification, the singular forms "a," "an" and "the" include plural referents unless the context clearly dictates otherwise.

As used herein, the term "patient" or "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

Chemical moieties referred to as univalent chemical moieties (e.g., alkyl, aryl, and the like) also encompass structurally permissible multivalent moieties, as understood by those skilled in the art. For example, while an "alkyl" moiety generally refers to a monovalent radical (e.g., $CH_3CH_2$—), in appropriate circumstances an "alkyl" moiety can also refer to a divalent radical (e.g., —CH$_2$CH$_2$—, which is equivalent to an "alkylene" group). Similarly, under circumstances where a divalent moiety is required, those skilled in the art will understand that the term "aryl" refers to the corresponding divalent arylene group.

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, C$_1$-C$_6$alkoxycarbonyloxy and —OC(O)C$_1$-C$_6$alkyl indicate the same functionality; similarly arylalkyl and -alkylaryl indicate the same functionality.

All atoms are understood to have their normal number of valences for bond formation (e.g., 4 for carbon, 3 for N, 2 for O, and 2, 4, or 6 for S, depending on the atom's oxidation state). On occasion a moiety can be defined, for example, as (A)$_a$B, wherein a is 0 or 1. In such instances, when a is 0 the moiety is B and when a is 1 the moiety is AB.

Where a substituent can vary in the number of atoms or groups of the same kind (e.g., alkyl groups can be C$_1$, C$_2$, C$_3$, and the like), the number of repeated atoms or groups can be represented by a range (e.g., C$_1$-C$_6$ alkyl) which includes each and every number in the range and any and all sub ranges. For example, C$_1$-C$_3$ alkyl includes C$_1$, C$_2$, C$_3$, C$_{1-2}$, C$_{1-3}$, and C$_{2-3}$ alkyl.

"Alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-dec enyl, and 3,7-dimethylocta-2,6-dienyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3 (4H)-on-5-yl, 2H-benzo[b][1,4]oxazin3 (4H)-on-6-yl, 2H-benzo[b][1,4]oxazin3 (4H)-on-7-yl, 2H-benzo[b][1,4]oxazin3 (4H)-on-8-yl, benzo[d]oxazin-2 (3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2 (3H)-on-5-yl, benzo[d] thiazol-2 (3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

An "aralkyl" or "arylalkyl" group comprises an aryl group covalently attached to an alkyl group, either of which independently is optionally substituted. Preferably, the aralkyl group is aryl(C$_1$-C$_6$)alkyl, including, without limitation, benzyl, phenethyl, and naphthylmethyl.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo [3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

"Halogen" refers to a chloro, bromo, fluoro or iodo atom radical. The term "halogen" also contemplates terms "halo" or "halide".

The terms "haloalkyl", "haloalkenyl" and "haloalkoxy" refer to an alkyl, alkenyl or alkoxy group, as the case may be, which is substituted with one or more halogen atoms.

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the disclosure.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

"Hydroxyalkyl" refers to a branched or unbranched alkyl group bearing a hydroxy (—OH) group. Examples include hydroxymethyl (—CH$_2$OH, a C$_1$hydroxyalkyl) and 1-hydroxyethyl (—CHOHCH$_3$, a C$_1$hydroxyalkyl).

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

Compounds of the disclosure can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. The disclosure contemplates various stereoisomers and mixtures thereof, which are specifically included within the scope of the disclosure. Stereoisomers include enantiomers, diastereomers, and mixtures of enantiomers or diastereomers. Individual stereoisomers of compounds of the disclosure can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Also, moieties disclosed herein which exist in multiple tautomeric forms include all such forms encompassed by a given tautomeric structure.

"Pharmaceutically acceptable" means approved or approvable by a regulatory agency of the Federal or state government or listed in the U.S. Pharmacopoeia or other generally recognized pharmacopoeia for use in animals, and more particularly in humans. It can be material which is not biologically or otherwise undesirable, i.e., the material can be administered to an individual without causing any undesirable biological effects or interacting in a deleterious manner with any of the components of the composition in which it is contained.

The term "pharmaceutically acceptable salt" of a compound means a salt that is pharmaceutically acceptable and that possesses the desired pharmacological activity of the parent compound. Such salts include, for example, acid addition salts and base addition salts.

"Acid addition salts" according to the disclosure, are formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

"Base addition salts" according to the disclosure are formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature can cause a single crystal form to dominate.

The term "agonist" refers to a compound that can combine with a GPR124 receptor to produce or increase a cellular activity. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the GPR124 receptor.

The term "activate", and variations thereof, refers to any measurable increase in cellular activity.

The term "antagonist" refers to a compound that can combine with a GPR124 receptor to reduce or inhibit a cellular activity. An antagonist may be a ligand that directly binds to the receptor. Alternatively, an antagonist may combine with a receptor indirectly by, for example, (a) forming a complex with another molecule that directly binds to the receptor, or (b) otherwise results in the modification of another compound so that the other compound directly binds to the GPR124 receptor.

Methods of Preparation

The compounds of the disclosure may be prepared by use of known chemical reactions and procedures. Representative methods for synthesizing compounds of the disclosure are presented below. It is understood that the nature of the substituents required for the desired target compound often determines the preferred method of synthesis. All variable groups of these methods are as described in the generic description if they are not specifically defined below.

General Procedure

Representative synthetic procedures for the preparation of compounds of the disclosure are outlined below in following schemes. Unless otherwise indicated, $R_1$-$R_4$, $R_8$, $R_9$, $R_{11}$-$R_{14}$, $R_{18}$, $R_{19}$, X, m and n and carry the definitions set forth above in connection with the above formulae.

Scheme 1

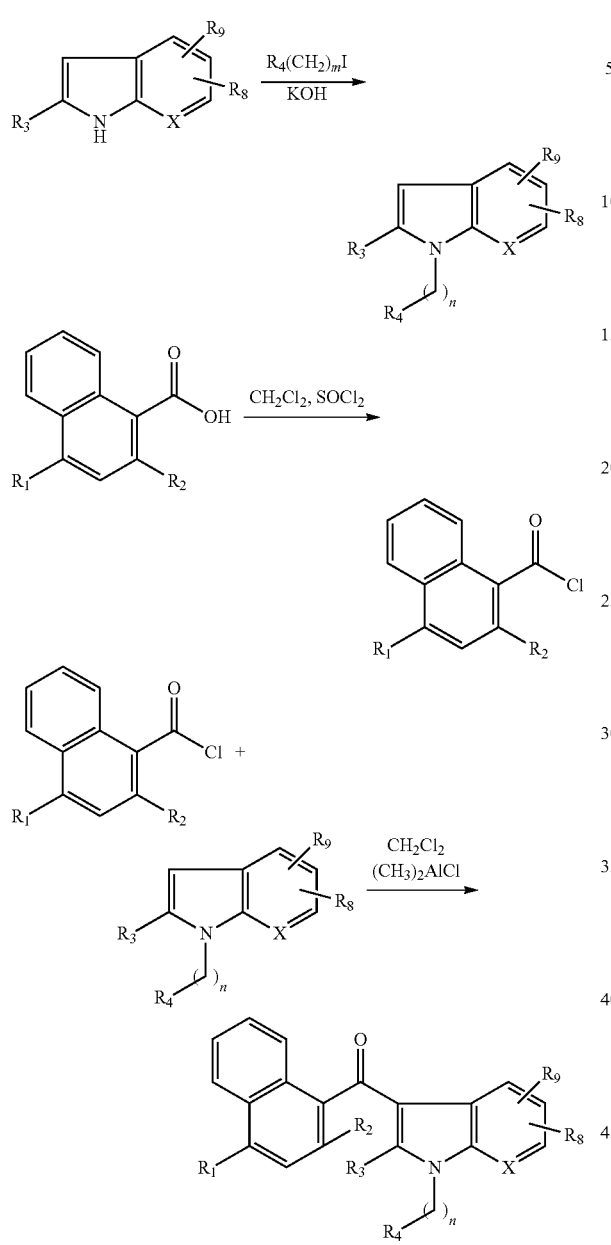

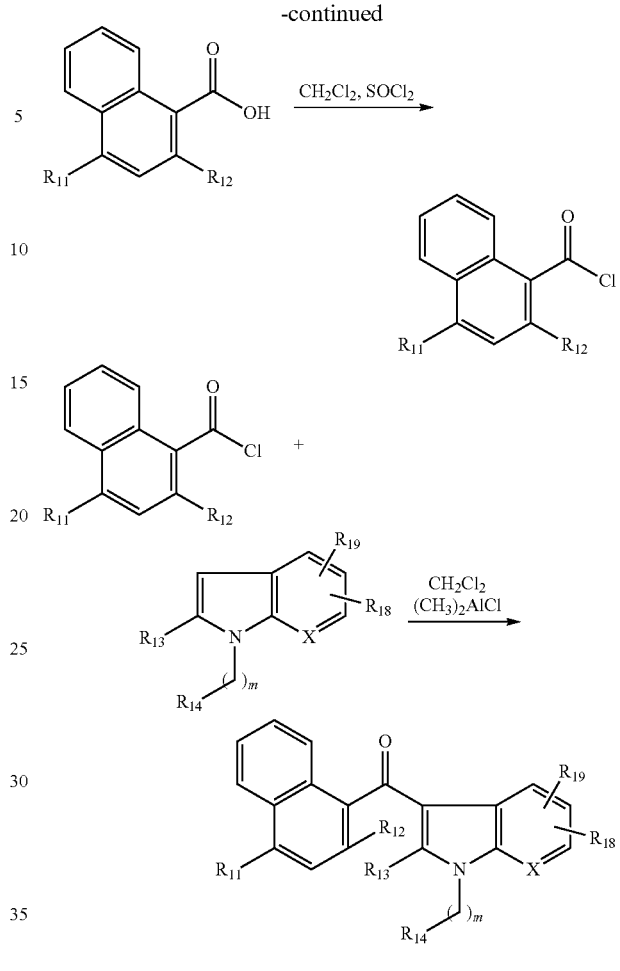

Scheme 2

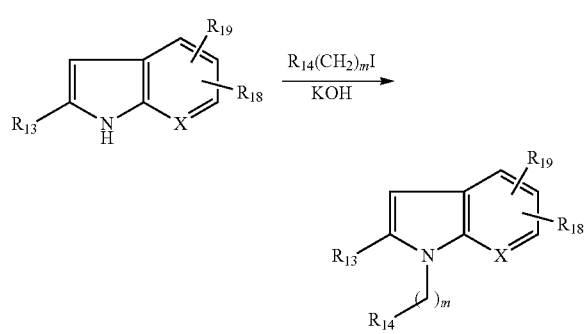

EXAMPLES

The preparation and utility of the compounds of the disclosure is illustrated further by the following examples, which are not to be construed as limiting the disclosure in scope or spirit to the specific procedures and compounds described in them. In all cases, unless otherwise specified, the column chromatography is performed using a silica gel solid phase.

Those having skill in the art will recognize that the starting materials and reaction conditions may be varied, the sequence of the reactions altered, and additional steps employed to produce compounds encompassed by the disclosure, as demonstrated by the following examples. Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Starting materials can be obtained from commercial sources or prepared by well-established literature methods known to those of ordinary skill in the art. The reactions are performed in a solvent appropriate to the reagents and materials employed and suitable for the transformations being effected. It will be understood by those skilled in the art of organic synthesis that the functionality present on the molecule should be consistent with the transformations proposed.

This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

Chemical names in this document were generated using Chemdraw Ultra Version 10.0 or Version 12.0, commercially available from CambridgeSoft.

Materials

DMSO (dimethyl sulfoxide), Trypsin-EDTA (0.25%), HEPES, $NaHCO_3$, KCl, $CaCl_2$, $MgSO_4$, glucose, NaOH and Triton X-100 were all purchased from Sigma-Aldrich (St. Louis, Mo.). NaCl, HCl (hydrochloric acid), and EDTA were purchased from Fisher Scientific (Santa Clara, Calif.). $NaH_2PO_4$ was purchased from JT Baker Analytical (Batavia, Ill.).

Drugs.

[$^3$H]-CP55,940 ((−)cis-3-[2-Hydroxy-4-(1,1-dimethyl-[2,3,4,4-$^3H_4$]-heptyl)phenyl]-trans-4R-3(hydroxypropyl)-1R-cyclohexanol) (0.54 mCi/ml), and CP55,940, $\Delta^9$-THC, was provided by the National Institute of Drug Abuse Drug Supply Program (RTI, Research Triangle Park, N.C.). WIN55,212-2 was from Cayman Chemicals (Ann Arbor, Mich.). HU-210 was purchased from Tocris Bioscience (Ellisville, Mo.). Pravadoline was obtained from Biomol. Research Laboratories, Inc (Philadelphia, Pa.). JWH-042, JWH-043, JWH-120, JWH-148, JWH-370, JWH-450 and JWH-451 were provided by Dr. John W. Huffman (Clemson University, Clemson, S.C.). All drugs were dissolved in DMSO, unless otherwise stated and stored at −20° C. until used for experiments.

Example 1

Synthesis of JWH451

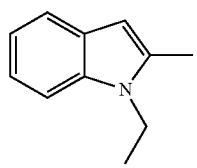

1-Ethyl-2-methylindole

To a mixture of 0.20 g (1.52 mmol) of 2-methylindole, 0.38 g (6.89 mmol) of KOH in DMSO (6 mL) was added 0.24 mL (3.04 mmol) of iodoethane. The mixture was stirred at room temperature for 12 hours, quenched by the addition of 15 mL of $H_2O$, and extracted with ethyl acetate (2×15 mL). The combined organic extracts were washed with water (10 mL), brine (20 mL), dried ($MgSO_4$), filtered and concentrated in vacuo. The crude product was purified by column chromatography (ether/petroleum ether 0.5:9.5) to give 0.20 g (83%) of the desired product as a red oil.

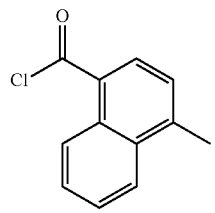

4-Methyl-1-napthoyl chloride

To a solution of 0.35 g (1.89 mmol) of 4-methyl-1-naphoic acid in 3 mL of dry dichloromethane under argon, was added 2.5 ml (34.3 mmol) of thionyl chloride. The solution was refluxed for 4 hrs and the solvent and excess thionyl chloride were removed by vacuum distillation to give a red oil, which was used without further purification.

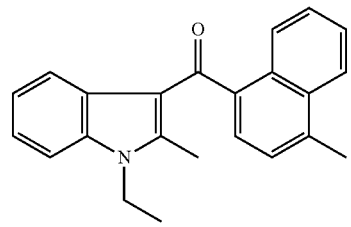 [SMILES: CCn1c(C)c(C(=O)c2ccc(C)c3ccccc23)c2ccccc21]

1-Ethyl-2-methyl-3-(4-methyl-1-napthoyl)indole

To a solution of 0.20 g (1.26 mmol) of 1-ethyl-2-methylindole in 4 mL of dry dichloromethane at 0° C. under argon, was added dropwise 0.17 g (1.89 mmol) of dimethylaluminum chloride. The solution was stirred at this temperature for 45 min and then 0.39 g (1.88 mmol) of 4-methyl-1-napthoyl chloride in 6 mL of dry dichloromethane was added, and the solution stirred at 0° C. for 4 hrs. The solution was carefully quenched by the addition of 1M HCl and extracted with dichloromethane (2×20 mL). The combined organic extract were washed with a saturated solution of $NaHCO_3$, $H_2O$, brine, dried ($MgSO_4$), filtered and concentrated in vacuo. The oil was purified by chromatography (ethyl acetate/petroleum ether 1:9) to afford the desired compound as an orange solid 0.16 g (40%), recrystallization from petroleum ether/ether provided white crystals, mp 136-137° C.: $^1$H NMR (300 MHz, $CDCl_3$) δ 1.42 (t, J=7.3 Hz, 3H), 2.51 (s, 3H), 2.80 (s, 3H), 4.25 (q, J=7.3 Hz, 2H), 6.92-7.05 (m, 1H), 7.17-7.29 (m, 2H), 7.32-7.39 (m, 2H), 7.46-7.53 (m, 2H), 7.54-7.61 (m, 1H), 8.11 (d, J=8.3 Hz, 1H), 8.21 (d, J=8.3 Hz, 1H); $^{13}$C NMR (300 MHz, $CDCl_3$) δ 12.3, 14.75, 19.9, 38.0, 109.2, 115.1, 121.4, 121.9, 122.2, 124.3, 125.8, 126.1, 126.3, 126.5, 127.3, 130.5, 132.9, 135.6, 136.7, 138.9, 145.1, 193.6; GC/MS (EI) m/z (rel intensity) 327 (100), 312 (80), 186 (60), 115 (20).

Anal. Calcd for $C_{23}H_{21}NO$: C, 84.37; H, 6.46; N, 4.28. Found $C_{23}H_{21}NO$: C, 84.23; H, 6.48; N, 4.29.

Example 2

Synthesis of TK18

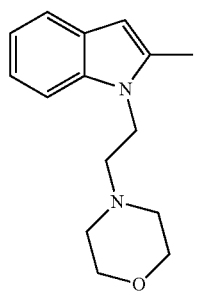 [SMILES: Cc1cc2ccccc2n1CCN1CCOCC1]

N-(2-(N-morpholinoethyl)-2-methylindole

A solution of 2-methyl indole (1.31 g, 10 mmol) in N,N-Dimethylformamide (10 mL) was added drop wise to a suspension of sodium hydride (0.6 g, 60% dispersion in mineral oil, 15 mmol) in N,N-Dimethylformamide (6 mL) and stirred for 30 minutes. A solution of 4-(2-methanesulfonyloxyethyl) morpholine (2.51 mmol, 12 mmol) was added at room temperature and stirred overnight. The reaction mixture was diluted with water (50 mL) and extracted with dichloromethane (3×30 mL). The combined organic extract was dried under magnesium sulfate and concentrated under reduced pressure. The product was purified by flash chromatography over silica gel eluting with 2% v/v methanol/dichloromethane. Yield 1.05 g, (43%).

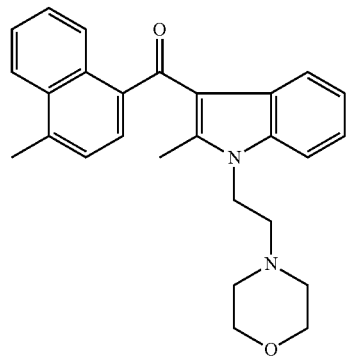 [SMILES: Cc1ccc(C(=O)c2c(C)n(CCN3CCOCC3)c3ccccc23)c2ccccc12]

3-(4-Methynaphthoyl N-(2-(N-morpholinoethyl)-2-methyl indole (TK18)

A solution of N-(2-(N-morpholinoethyl)-2-methylindole (600 mg, 2.45 mmol) in dichloromethane (4 mL) was added at 0° C. to a suspension of aluminum chloride (1.0 gram, 7.35 mmol) and 4-methyl naphthoylchloride (1.5 g; 7.35 mmol) in dichloromethane (25 mL) and stirred for 1 h at 0° C. The reaction mixture was warmed to room temperature and stirred overnight. Saturated ammonium chloride solution (25 mL) was added, and the reaction mixture was extracted with dichloromethane (3×50 mL). The combined organic extract was dried over anhydrous magnesium sulfate and concentrated under reduced pressure. The product was purified by flash chromatography over silica gel eluting with 0.5% v/v methanol/dichloromethane. Final purification by recrystallization from 10% v/v ethyl acetate/hexane gave a final yield of 0.20 g, (25%). $^1$H NMR ($d_6$DMSO, δ) 8.20 (d, J=8.4 Hz, 1H), 8.11 (d, J=8.4 Hz, 1H), 7.01-7.59 (m, 8H), 4.28 (t, J=7.2 Hz, 2H), 3.72 (t, J=4.5 Hz, 4H), 2.80 (s, 3H), 2.72 (t, J=7.2 Hz, 2H), 2.51 (br.s. 8H overlapping DMSO. MS m/z 413.5 [M+H]$^+$, 435.5 [M+Na]$^+$.

Example 3

Synthesis of CBX001

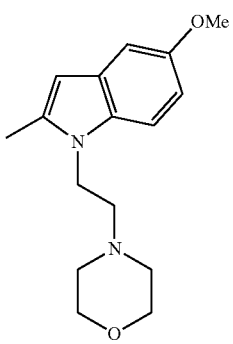 [SMILES: COc1ccc2c(c1)cc(C)n2CCN1CCOCC1]

4-(2-(5-methoxy-2-methyl-1H-indol-1-yl)ethyl)morpholine

To a solution of 2-chloroethylmorpholine HCl (138 mg, 0.74 mmol) in 0.3 mL DMSO was added pulverized KOH (104 mg, 1.86 mmol), then after 5 min, a solution of 5-methoxy-2-methylindole (138 mg, 0.74 mmol) in 0.2 mL DMSO was added and the reaction stirred at room temperature overnight. The reaction mixture was partitioned between $H_2O$ and toluene, and the organic extract washed two times with $H_2O$, dried over $MgSO_4$, filtered, and concentrated in vacuo. The crude product was purified via silica gel chromatography using a gradient from 0 to 5% MeOH in $CH_2Cl_2$ to give a final yield of 120 mg (0.44 mmol). $^1$H NMR (500 MHz, CDCl$_3$, δ): 2.47 (s, 3H), 2.49-2.62 (m, 4H), 2.66 (t, J=7.3 Hz, 2H), 3.76 (t, J=4.5 Hz, 4H), 3.89 (s, 3H), 4.18 (t, J=7.3 Hz, 2H), 6.22 (s, 1H), 6.86 (dd, J=8.8 Hz, 2.4 Hz, 1H), 7.06 (d, J=2.3 Hz, 1H), 7.21 (d, J=8.8 Hz, 1H). $^{13}$C NMR (500 MHz, CDCl$_3$, δ): 12.89, 41.12, 54.15, 55.91, 58.01, 66.98, 99.87, 102.01, 109.45, 110.32, 128.53, 131.82, 137.06, 154.05. MS m/z 275.3 [M+H]$^+$.

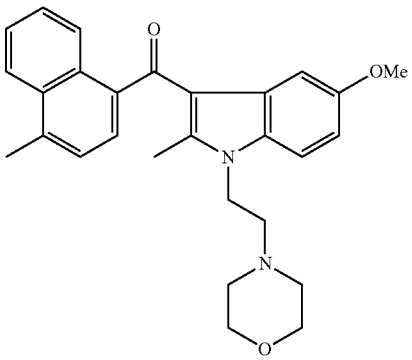 [SMILES: COc1ccc2c(c1)c(C(=O)c1ccc(C)c3ccccc13)c(C)n2CCN1CCOCC1]

(5-methoxy-2-methyl-1-(2-morpholinoethyl)-1H-indol-3-yl)(4-methylnaphthalen-1-yl)methanone (CBX001)

To a solution of 4-methyl-1-naphthoyl chloride (84 mg, 0.41 mmol) and 4-(2-(5-methoxy-2-methyl-1H-indol-1-yl)ethyl)morpholine (120 mg, 0.44 mmol) in 8 mL CH$_2$Cl$_2$ at −70° C. was added dropwise ethyl aluminum dichloride (0.5 mL, 0.90 mmol, 1.8 M in toluene). The reaction mixture was allowed to slowly warm to room temperature overnight. The reaction mixture was then partitioned between ethyl acetate and cold H$_2$O, and the aqueous layer extracted twice with ethyl acetate. The combined organic extract was washed successively with H$_2$O, 10% K$_2$CO$_3$, and brine, dried over MgSO$_4$, filtered, and concentrated in vacuo. The crude product was purified via silica gel chromatography using a gradient from 0 to 10% MeOH in CH$_2$Cl$_2$ to give CBX001 (107 mg, 0.24 mmol). $^1$H NMR (500 MHz, CDCl$_3$, δ): 2.37 (s, 3H), 2.42-2.55 (m, 4H), 2.66 (t, J=6.9 Hz, 2H), 2.78 (s, 3H), 3.59 (s, 3H), 3.68 (t, J=4.2 Hz, 4H), 4.17 (t, J=6.9 Hz, 2H), 6.84 (dd, J=8.8 Hz, 2.4 Hz, 1H), 6.92 (d, J=2.2 Hz, 1H), 7.20 (d, J=8.8 Hz, 1H), 7.38 (d, J=7.0 Hz, 1H), 7.41-7.50 (m, 2H), 7.55 (t, J=7.2 Hz, 1H), 8.08 (d, J=8.4 Hz, 1H), 8.15 (d, J=8.3 Hz, 1H). $^{13}$C NMR (500 MHz, CDCl$_3$, δ): 13.14, 20.21, 41.74, 53.90, 54.49, 55.80, 57.81, 67.29, 103.91, 110.33, 112.67, 115.61, 124.69, 125.76, 126.30, 126.59, 126.91, 128.42, 130.86, 131.35, 133.25, 136.92, 139.50, 145.98, 156.28, 193.91. MS m/z 443.4 [M+H]$^+$.

Example 4

Synthesis of CBX002

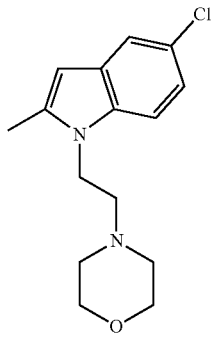 [SMILES: Cc1cc2cc(Cl)ccc2n1CCN1CCOCC1]

4-(2-(5-chloro-2-methyl-1H-indol-1-yl)ethyl)morpholine

To a solution of 2-chloroethylmorpholine HCl (100 mg, 0.60 mmol) in 0.3 mL DMSO was added pulverized KOH (102 mg, 1.81 mmol), then after 10 min, a solution of 5-chloro-2-methylindole (134 mg, 0.72 mmol) in 0.2 mL DMSO was added and the reaction stirred at room temperature overnight. Additional 2-chloroethylmorpholine (22 mg, 0.12 mmol) and KOH (17 mg, 0.3 mmol) added and stirred overnight. The reaction mixture was partitioned between H$_2$O and toluene, and the organic extract washed two times with H$_2$O, dried over MgSO$_4$, filtered, and concentrated in vacuo. The crude product was purified via silica gel chromatography using a gradient from 0 to 5% MeOH in CH$_2$Cl$_2$ to give a final yield of 154 mg (0.55 mmol). $^1$H NMR (500 MHz, CDCl$_3$, δ): 2.47 (s, 3H), 2.48-2.57 (m, 4H), 2.63 (t, J=7.2 Hz, 2H), 3.73 (t, J=4.4 Hz, 4H), 4.16 (t, J=7.2 Hz, 2H), 6.20 (s, 1H), 7.11 (dd, J=8.6 Hz, 1.7 Hz, 1H), 7.19 (d, J=8.6 Hz, 1H), 7.50 (d, J=1.5 Hz, 1H). $^{13}$C NMR (500 MHz, CDCl$_3$, δ): 12.88, 41.23, 54.13, 57.86, 66.95, 99.88, 109.78, 119.15, 120.64, 124.97, 129.18, 134.99, 138.03. MS m/z 279.3 [M+H]$^+$.

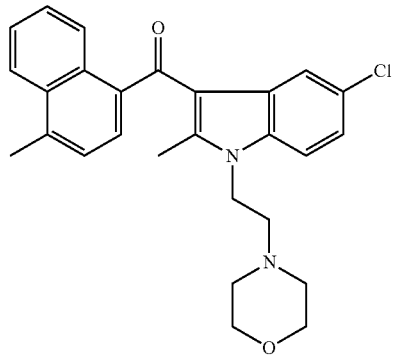 [SMILES: Cc1ccc(C(=O)c2c(C)n(CCN3CCOCC3)c3ccc(Cl)cc23)c2ccccc12]

(5-chloro-2-methyl-1-(2-morpholino ethyl)-1H-indol-3-yl)(4-methylnaphthalen-1-yl)methanone (CBX002)

To a solution of 4-methyl-1-naphthoyl chloride (106 mg, 0.52 mmol) and 4-(2-(5-chloro-2-methyl-1H-indol-1-yl)ethyl)morpholine (154 mg, 0.55 mmol) in 8 mL CH$_2$Cl$_2$ at −70° C. was added dropwise ethyl aluminum dichloride (0.63 mL, 1.14 mmol, 1.8 M in toluene). The reaction mixture was allowed to slowly warm to room temperature overnight. The reaction mixture was then partitioned between ethyl acetate and cold H$_2$O, and the aqueous layer extracted twice with ethyl acetate. The combined organic extract was washed successively with H$_2$O, 10% K$_2$CO$_3$, and brine, dried over MgSO$_4$, filtered, and concentrated in vacuo. The crude product was purified via silica gel chromatography using a gradient from 0 to 10% MeOH in CH$_2$Cl$_2$ to give CBX002 (141 mg, 0.32 mmol). $^1$H NMR (500 MHz, CDCl$_3$, δ): 2.32 (s, 3H), 2.47 (t, J=4.3 Hz, 4H), 2.66 (t, J=6.9 Hz, 2H), 2.79 (s, 3H), 3.68 (t, J=4.4 Hz, 4H), 4.19 (t, J=6.9 Hz, 2H), 7.14-7.21 (m, 1H), 7.23 (d, J=8.6 Hz, 1H), 7.36 (d, J=7.2 Hz, 1H), 7.43-7.52 (m, 2H), 7.58 (t, J=7.6 Hz, 1H), 7.61 (d, J=1.8 Hz, 1H), 8.10 (d, J=8.4 Hz, 1H), 8.18 (d, J=8.4 Hz, 1H). $^{13}$C NMR (500 MHz, CDCl$_3$, δ): 12.69, 19.92, 41.47, 54.08, 57.34, 66.87, 110.25, 115.09, 121.16, 122.69, 124.45, 125.75, 125.99, 126.06, 126.23, 126.66, 127.98, 128.34, 130.46, 132.95, 134.43, 137.27, 138.21, 146.37, 193.24. MS m/z 447.5 [M+H]$^+$.

Example 5

Synthesis of CBX003

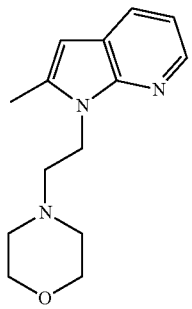 [SMILES: Cc1cc2cccnc2n1CCN1CCOCC1]

4-(2-(2-methyl-1H-pyrrolo[2,3-b]pyridin-1-yl)ethyl)morpholine

To a solution of 2-chloroethylmorpholine HCl (169 mg, 0.91 mmol) in 0.3 mL DMSO was added pulverized KOH (128 mg, 2.27 mmol), then after 10 min, a solution of 2-methyl-7-azaindole (100 mg, 0.76 mmol) in 0.2 mL DMSO was added and the reaction stirred at room temperature overnight. The reaction mixture was partitioned between $H_2O$ and toluene, and the organic extract washed two times with $H_2O$, dried over $MgSO_4$, filtered, and concentrated in vacuo. The crude product was purified via silica gel chromatography using a gradient from 0 to 10% MeOH in $CH_2Cl_2$ to give a final yield of 144 mg (0.59 mmol). $^1$H NMR (500 MHz, $CDCl_3$, δ): 2.46 (s, 3H), 2.47-2.58 (m, 4H), 2.67 (t, J=7.0 Hz, 2H), 3.66 (t, J=4.5 Hz, 4H), 4.33 (t, J=7.0 Hz, 2H), 6.15 (s, 1H), 6.87-7.09 (m, 1H), 7.73 (dd, J=7.7 Hz, 1.3 Hz, 1H), 8.19 (dd, J=4.6 Hz, 1.3 Hz, 1H). $^{13}$C NMR (500 MHz, $CDCl_3$, δ): 13.51, 39.75, 54.37, 58.49, 67.18, 98.40, 116.05, 121.09, 127.47, 137.78, 141.71, 148.56. MS m/z 246.1 $[M+H]^+$.

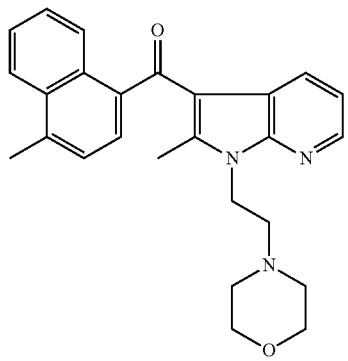 [SMILES: Cc1ccc(C(=O)c2c(C)n(CCN3CCOCC3)c3ncccc23)c2ccccc12]

(2-methyl-1-(2-morpholino ethyl)-1H-pyrrolo[2,3-b]pyridin-3-yl)(4-methylnaphthalen-1-yl)methanone (CBX003)

To a solution of 4-methyl-1-naphthoyl chloride (112 mg, 0.55 mmol) and 4-(2-(2-methyl-1H-pyrrolo[2,3-b]pyridin-1-yl)ethyl)morpholine (143 mg, 0.59 mmol) in 2.5 mL $CH_2Cl_2$ at −70° C. was added dropwise ethyl aluminum dichloride (0.67 mL, 1.21 mmol, 1.8 M in toluene). The reaction mixture was allowed to slowly warm to room temperature overnight. The reaction mixture was then partitioned between ethyl acetate and cold $H_2O$, and the aqueous layer extracted twice with ethyl acetate. The combined organic extract was washed successively with $H_2O$, 10% $K_2CO_3$, and brine, dried over $MgSO_4$, filtered, and concentrated in vacuo. The crude product was purified via silica gel chromatography using a gradient from 0 to 5% MeOH in $CH_2Cl_2$, then taken up in $CHCl_3$ and washed with a saturated solution of $Na_2CO_3$, dried over $Na_2SO_4$, filtered, and concentrated in vacuo to give CBX003 (32 mg, 0.077 mmol). $^1$H NMR (500 MHz, $CDCl_3$, δ): 2.46-2.58 (m, 4H), 2.60 (s, 3H), 2.78 (t, J=6.8 Hz, 2H), 2.81 (s, 3H), 3.69 (t, J=4.5 Hz, 4H), 4.47 (t, J=6.8 Hz, 2H), 6.91-7.02 (m, 1H), 7.38 (d, J=7.2 Hz, 1H), 7.43 (dd, J=7.9 Hz, 1.4 Hz, 1H), 7.45-7.52 (m, 2H), 7.58 (td, J=7.6 Hz, 1.1 Hz, 1H), 8.11 (d, J=8.4 Hz, 1H), 8.16 (d, J=8.4 Hz, 1H), 8.26 (dd, J=4.7 Hz, 1.5 Hz, 1H). $^{13}$C NMR (500 MHz, $CDCl_3$, δ): 12.83, 19.93, 39.55, 53.99, 57.68, 66.93, 113.29, 118.10, 119.85, 124.42, 125.76, 125.78, 126.06, 126.24, 126.66, 129.10, 130.36, 132.90, 137.15, 138.40, 143.02, 146.42, 147.59, 193.21. MS m/z 415.5 $[M+H]^+$.

Example 6

Synthesis of CBX004

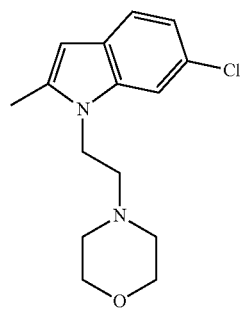 [SMILES: Cc1cc2ccc(Cl)cc2n1CCN1CCOCC1]

4-(2-(6-chloro-2-methyl-1H-indol-1-yl)ethyl)morpholine

To a solution of 2-chloroethylmorpholine HCl (134 mg, 0.72 mmol) in 0.3 mL DMSO was added pulverized KOH (102 mg, 1.81 mmol), then after 10 min, a solution of 6-chloro-2-methylindole (100 mg, 0.60 mmol) in 0.2 mL DMSO was added and the reaction stirred at room temperature overnight. Additional 2-chloroethylmorpholine (22 mg, 0.12 mmol) and KOH (17 mg, 0.3 mmol) added and stirred overnight. The reaction mixture was partitioned between $H_2O$ and toluene, and the organic extract washed two times with $H_2O$, dried over $MgSO_4$, filtered, and concentrated in vacuo. The crude product was purified via silica gel chromatography using a gradient from 0 to 50% ethyl acetate in hexane to give a final yield of 149 mg (0.54 mmol). $^1$H NMR (500 MHz, $CDCl_3$, δ): 2.44 (s, 3H), 2.49 (t, J=4.4 Hz, 4H), 2.62 (t, J=7.2 Hz, 2H), 3.73 (t, J=4.5 Hz, 4H), 4.11 (t, J=7.2 Hz, 2H), 6.23 (s, 1H), 7.06 (dd, J=8.4 Hz, 1.7 Hz, 1H), 7.28 (s, 1H), 7.42 (d, J=8.3 Hz, 1H). $^{13}$C NMR (500 MHz, $CDCl_3$, δ): 12.79, 41.18, 54.11, 57.83, 67.5, 100.30, 108.95, 119.90, 120.53, 126.40, 126.70, 137.06, 137.37. MS m/z 279.3 $[M+H]^+$.

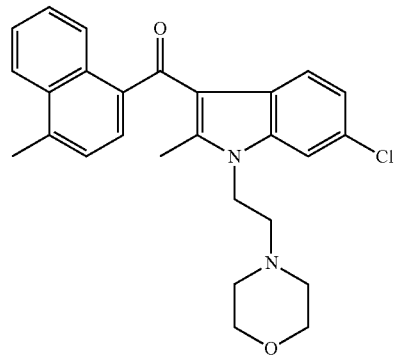 [SMILES: Cc1ccc(C(=O)c2c(C)n(CCN3CCOCC3)c3cc(Cl)ccc23)c2ccccc12]

(6-chloro-2-methyl-1-(2-morpholinoethyl)-1H-indol-3-yl)(4-methylnaphthalen-1-yl)methanone (CBX004)

To a solution of 4-(2-(6-chloro-2-methyl-1H-indol-1-yl)ethyl)morpholine (48 mg, 0.17 mmol) in 0.5 mL CH$_2$Cl$_2$ at 0° C. was added dropwise ethyl aluminum dichloride (0.14 mL, 0.26 mmol, 1.8 M in toluene). The reaction mixture was stirred at 0° C. for 30 min, then a solution of 4-methyl-1-naphthoyl chloride (43 mg, 0.21 mmol) in 0.5 mL CH$_2$Cl$_2$ was added and stirred at 0° C. for 1 h, then allowed to slowly warm to room temperature overnight. The reaction stirred at room temp for 3 d. The reaction mixture was then poured into ice cold 1M HCl and extracted three times with CH$_2$Cl$_2$. The combined organic extract was washed three times with a saturated solution of sodium bicarbonate, dried over MgSO$_4$, filtered, and concentrated in vacuo. The crude product was purified via silica gel chromatography using a gradient from 0 to 5% MeOH in CH$_2$Cl$_2$ to give CBX004 (23 mg, 0.052 mmol). $^1$H NMR (500 MHz, CDCl$_3$, δ): 2.46 (s, 3H), 2.48-2.59 (m, 4H), 2.71 (t, J=6.9 Hz, 2H), 2.80 (s, 3H), 3.71 (t, J=4.6 Hz, 4H), 4.20 (t, J=6.9 Hz, 2H), 7.02 (dd, J=8.6 Hz, 1.8 Hz, 1H), 7.25 (d, J=8.6 Hz, 1H), 7.33 (d, J=1.7 Hz, 1H), 7.37 (d, J=7.2 Hz, 1H), 7.44-7.53 (m, 2H), 7.58 (td, J=7.6 Hz, 1.1 Hz, 1H), 8.11 (d, J=8.4 Hz, 1H), 8.18 (d, J=8.4 Hz, 1H). $^{13}$C NMR (500 MHz, CDCl$_3$, δ): 12.62, 19.93, 41.40, 54.10, 57.36, 66.88, 109.40, 115.34, 122.34, 122.49, 124.40, 125.72, 125.76, 126.03, 126.08, 126.21, 126.66, 128.25, 130.43, 132.91, 136.51, 137.22, 138.35, 146.00, 193.43. MS m/z 447.6 [M+H]$^+$.

Example 7

Synthesis of CBX005

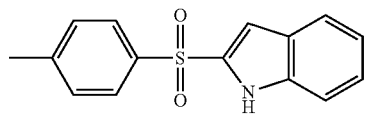 [SMILES: Cc1ccc(S(=O)(=O)c2cc3ccccc3[nH]2)cc1]

2-tosyl-1H-indole

To a solution of indole (586 mg, 5.0 mmol) in 10 mL THF at −70° C. was added n-butyl lithium (3.7 mL, 5.1 mmol, 1.39 M in hexane) dropwise over 35 min keeping the temperature below −65° C. The reaction was stirred at −70° C. for 30 min, then a saturated solution of CO$_2$ in 20 mL THF added by cannula, the dry ice bath removed and the reaction mixture bubbled with CO$_2$ as the reaction warmed to room temperature. The reaction mixture was concentrated in vacuo then taken up in 10 mL THF and cooled to −70° C. To the solution was added tert-butyl lithium (3 mL, 5.17 mmol, 1.7 M in pentane) dropwise and stirred at −70° C. 1 h, then the reaction mixture added by cannula to a solution of p-toluenesulfonyl fluoride (1.74 g, 10 mmol) in 10 mL THF and stirred at −70° C. 2 h. The reaction was quenched with 1 mL H$_2$O, poured into a solution of ammonium chloride (pH 5), and extracted twice with CHCl$_3$. The combined organic extract was washed successively with a saturated solution of sodium bicarbonate and brine, dried over MgSO$_4$, filtered, and concentrated in vacuo. The crude product was purified via silica gel chromatography using a gradient from 2 to 20% ethyl acetate in hexanes to give a final yield of 199 mg (0.73 mmol). $^1$H NMR (500 MHz, CDCl$_3$, δ): 2.41 (s, 3H), 7.16-7.26 (m, 2H), 7.27-7.33 (m, 2H), 7.35 (t, J=7.3 Hz, 1H), 7.45 (d, J=8.4 Hz, 1H), 7.69 (d, J=8.1 Hz, 1H), 7.93 (d, J=8.3 Hz, 2H), 9.31 (s, 1H). $^{13}$C NMR (500 MHz, CDCl$_3$, δ): 21.61, 108.87, 112.39, 121.52, 122.62, 125.95, 127.08, 127.35, 130.02, 134.45, 137.16, 138.53, 144.57.

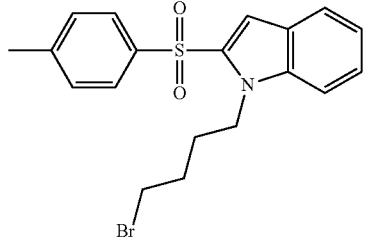 [SMILES: Cc1ccc(S(=O)(=O)c2cc3ccccc3n2CCCCBr)cc1]

1-(4-bromobutyl)-2-tosyl-1H-indole

To a solution of 2-tosyl-1H-indole (199 mg, 0.73 mmol) in 3 mL DMF was added 1,4-dibromobutane (263 μL, 2.20 mmol) in 1 mL DMF and KOH (41 mg, 0.73 mmol), and the reaction stirred at room temperature 1.75 h. The reaction mixture was then partitioned between water and ether, and the aqueous layer extracted twice with ether. The combined organic extract was washed with water, dried over MgSO$_4$, filtered, and concentrated in vacuo. The crude product was purified via silica gel chromatography using a gradient from 0 to 15% ethyl acetate in hexanes to give a final yield of 178 mg (0.44 mmol). $^1$H NMR (500 MHz, CDCl$_3$, δ): 1.66-1.81 (m, 2H), 1.81-1.94 (m, 2H), 2.44 (s, 3H), 3.34 (t, J=6.4 Hz, 2H), 4.35 (t, J=7.6 Hz, 2H), 7.21 (t, J=7.0 Hz, 1H), 7.30-7.44 (m, 5H), 7.73 (d, J=7.9 Hz, 1H), 7.87 (d, J=8.1 Hz, 2H). $^{13}$C NMR (500 MHz, CDCl$_3$, δ): 22.07, 29.04, 30.26, 33.26, 44.41, 111.08, 111.49, 121.67, 123.42, 125.83, 126.19, 128.09, 130.44, 135.22, 138.78, 139.12, 145.08. MS m/z 406.3 [M+H]$^+$.

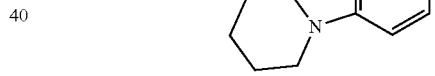

6,7,8,9-tetrahydropyrido[1,2-a]indole

To a refluxing solution of 1-(4-bromobutyl)-2-tosyl-1H-indole (178 mg, 0.44 mmol) in 9.5 mL toluene was added dropwise over 5 min a mixture of tributyltin hydride (285 μL, 1.06 mmol) and 2,2'-azobisisobutyronitrile (14 mg, 0.088 mmol) in 22.5 mL toluene. The reaction mixture was refluxed 2 h, then concentrated in vacuo. To the crude product was added 125 μL H$_2$O, 3 mL ethyl acetate, and 150 mg KF and stirred at room temperature overnight. Potassium carbonate was added and the mixture filtered and concentrated in vacuo. The process was repeated with another 125 μL H$_2$O, 3 mL ethyl acetate, and 150 mg KF and stirred at room temperature 2 h. Potassium carbonate added and the mixture filtered and concentrated in vacuo. The crude product was purified via silica gel chromatography using a gradient from 0 to 10% ethyl acetate in hexanes to give a final yield of 58 mg (0.34 mmol). $^1$H NMR (500 MHz, CDCl$_3$, δ): 1.89-2.05 (m, 2H), 2.10-2.24 (m, 2H), 3.06 (t, J=6.1 Hz, 2H), 4.11 (t, J=6.1 Hz, 2H), 6.29 (s, 1H), 7.18 (t, J=7.1 Hz, 1H), 7.23 (t, J=7.4 Hz, 1H), 7.35 (d, J=7.9 Hz, 1H), 7.63 (d, J=7.7 Hz, 1H). $^{13}$C NMR (500 MHz, CDCl$_3$, δ): 21.76, 23.93, 24.75, 42.78, 97.98, 109.03, 120.06, 120.58, 128.71, 136.76, 137.63. MS m/z 172 [M+H]$^+$.

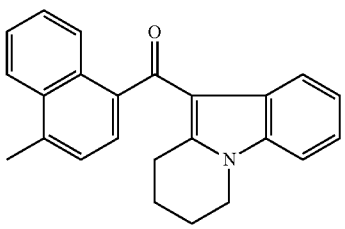 [SMILES: Cc1ccc(C(=O)c2c3n(c4ccccc24)CCCC3)c2ccccc12]

(4-methylnaphthalen-1-yl)(6,7,8,9-tetrahydropyrido[1,2-a]indol-10-yl)methanone (CBX005)

To a solution of 4-methyl-1-naphthoyl chloride (37 mg, 0.18 mmol) and 6,7,8,9-tetrahydropyrido[1,2-a]indole (30 mg, 0.18 mmol) in 1 mL $CH_2Cl_2$ at −70° C. was added dropwise ethyl aluminum dichloride (0.22 mL, 0.40 mmol, 1.8 M in toluene). The reaction mixture was allowed to slowly warm to room temperature and stirred for 3 d then cooled to −70° C. and 4-methyl-1-naphthoyl chloride (4 mg, 0.020 mmol) and ethyl aluminum dichloride (20 μL, 0.036 mmol) added and allowed to warm to room temperature and stirred 6 h. The reaction mixture was again cooled to −70° C. and 4-methyl-1-naphthoyl chloride (4 mg, 0.020 mmol) and ethyl aluminum dichloride (20 μL, 0.036 mmol) added and allowed to warm to room temperature overnight. It was again cooled to −70° C. and 4-methyl-1-naphthoyl chloride (8 mg, 0.040 mmol), ethyl aluminum dichloride (40 μL, 0.072 mmol), and 1 mL $CH_2Cl_2$ added and allowed to warm to room temperature overnight. The reaction mixture was then partitioned between ethyl acetate and cold $H_2O$, and the aqueous layer extracted twice with ethyl acetate. The combined organic extract was washed successively with $H_2O$, 10% $K_2CO_3$, and brine, dried over $MgSO_4$, filtered, and concentrated in vacuo. The crude product was purified via silica gel chromatography using a gradient from 0 to 25% ethyl acetate in hexanes to give CBX005 (22 mg, 0.065 mmol). $^1$H NMR (500 MHz, $CDCl_3$, δ): 1.80-1.95 (m, 2H), 2.05-2.33 (m, 2H), 2.82 (s, 3H), 2.97 (t, J=6.3 Hz, 2H), 4.13 (t, J=6.2 Hz, 2H), 7.09 (t, J=7.6 Hz, 1H), 7.22 (t, J=7.6 Hz, 1H), 7.30-7.37 (m, 2H), 7.40 (d, J=7.1 Hz, 1H), 7.43-7.52 (m, 2H), 7.58 (t, J=7.6 Hz, 1H), 8.08-8.19 (m, 2H). $^{13}$C NMR (500 MHz, $CDCl_3$, δ): 19.87, 20.03, 22.31, 25.20, 42.65, 108.94, 113.75, 121.25, 122.03, 122.44, 124.31, 124.99, 125.93, 126.05, 126.24, 126.41, 126.97, 130.34, 132.89, 136.27, 139.26, 147.09, 193.08. MS m/z 340.4 [M+H]$^+$.

Example 8

Synthesis of CBX006

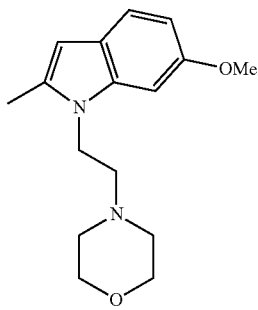 [SMILES: COc1ccc2cc(C)n(CCN3CCOCC3)c2c1]

4-(2-(6-methoxy-2-methyl-1H-indol-1-yl)ethyl)morpholine

To a solution of 2-chloroethylmorpholine HCl (138 mg, 0.74 mmol) in 0.3 mL DMSO was added pulverized KOH (104 mg, 1.86 mmol), then after 10 min, a solution of 6-methoxy-2-methylindole (138 mg, 0.74 mmol) in 0.2 mL DMSO was added and the reaction stirred at room temperature overnight. The reaction mixture was partitioned between $H_2O$ and toluene, and the organic extract washed two times with $H_2O$, dried over $MgSO_4$, filtered, and concentrated in vacuo. The crude product was purified via silica gel chromatography using a gradient from 0 to 10% MeOH in $CH_2Cl_2$ to give a final yield of 17 mg (0.062 mmol). $^1$H NMR (500 MHz, $CDCl_3$, δ): 2.45 (s, 3H), 2.50-2.63 (m, 4H), 2.67 (t, J=7.4 Hz, 2H), 3.71-3.83 (m, 4H), 3.90 (s, 3H), 4.18 (t, J=7.4 Hz, 2H), 6.19 (s, 1H), 6.78 (dd, J=8.5 Hz, 2.2 Hz, 1H), 6.81 (s, 1H), 7.42 (d, J=8.5 Hz, 1H). $^{13}$C NMR (500 MHz, $CDCl_3$, δ): 12.77, 40.98, 54.13, 55.92, 57.74, 66.94, 93.50, 99.82, 108.35, 120.26, 122.51, 135.31, 137.25, 155.53. MS m/z 275.3 [M+H]$^+$.

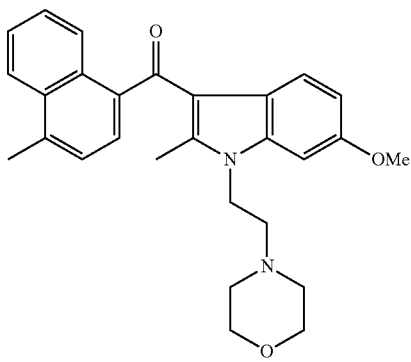 [SMILES: COc1ccc2c(C(=O)c3ccc(C)c4ccccc34)c(C)n(CCN3CCOCC3)c2c1]

(6-methoxy-2-methyl-1-(2-morpholinoethyl)-1H-indol-3-yl)(4-methylnaphthalen-1-yl)methanone (CBX006)

To a solution of 4-methyl-1-naphthoyl chloride (11 mg, 0.055 mmol) and 4-(2-(6-methoxy-2-methyl-1H-indol-1-yl)ethyl)morpholine (15 mg, 0.055 mmol) in 1 mL $CH_2Cl_2$ at −70° C. was added dropwise ethyl aluminum dichloride (70 μL, 0.12 mmol, 1.8 M in toluene). The reaction mixture was allowed to slowly warm to room temperature overnight. The reaction mixture was then partitioned between ethyl acetate and cold $H_2O$, and the aqueous layer extracted twice with ethyl acetate. The combined organic extract was washed successively with $H_2O$, 10% $K_2CO_3$, and brine, dried over $MgSO_4$, filtered, and concentrated in vacuo. The crude product was purified via silica gel chromatography using a gradient from 0 to 10% MeOH in $CH_2Cl_2$ to give CBX006 (4 mg, 0.009 mmol). $^1$H NMR (500 MHz, $CDCl_3$, δ): 2.46 (s, 3H), 2.50-2.63 (m, 4H), 2.72 (t, J=7.1 Hz, 2H), 2.81 (s, 3H), 3.73 (t, J=4.5 Hz, 4H), 3.87 (s, 3H), 4.23 (t, J=7.1 Hz, 2H), 6.72 (dd, J=8.7 Hz, 2.2 Hz, 1H), 6.83 (d, J=2.2 Hz, 1H), 7.23 (d, J=8.7 Hz, 1H), 7.38 (d, J=7.1 Hz, 1H), 7.44-7.54 (m, 2H), 7.58 (t, J=7.6 Hz, 1H), 8.11 (d, J=8.4 Hz, 1H), 8.19 (d, J=8.4 Hz, 1H). MS m/z 443.4 [M+H]$^+$.

Example 9

Synthesis of CBX007

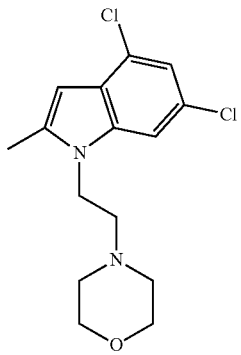 [SMILES: Cc1cc2c(Cl)cc(Cl)cc2n1CCN1CCOCC1]

4-(2-(4,6-dichloro-2-methyl-1H-indol-1-yl)ethyl)morpholine

To a solution of 4,6-dichloro-2-methylindole (75 mg, 0.37 mmol) in 0.5 mL DMSO was added pulverized KOH (95 mg, 1.69 mmol), then 2-chloroethylmorpholine HCl (140 mg, 0.75 mmol) and the reaction stirred at room temperature overnight. The reaction mixture was partitioned between $H_2O$ and toluene, and the organic extract washed two times with $H_2O$, dried over $MgSO_4$, filtered, and concentrated in vacuo. The crude product was purified via silica gel chromatography using a gradient from 0 to 10% MeOH in $CH_2Cl_2$ to give a final yield of 91 mg (0.29 mmol). $^1H$ NMR (500 MHz, $CDCl_3$, δ): 2.42-2.55 (m, 4H), 2.44 (s, 3H), 2.60 (t, J=7.0 Hz, 2H), 3.65-3.79 (m, 4H), 4.08 (t, J=7.0 Hz, 2H), 6.31 (s, 1H), 7.09 (s, 1H), 7.16 (s, 1H). $^{13}C$ NMR (500 MHz, $CDCl_3$, δ): 12.84, 41.59, 54.10, 57.79, 66.91, 98.99, 107.84, 119.47, 125.23, 125.51, 126.17, 137.22, 138.20. MS m/z 313.5 $[M+H]^+$.

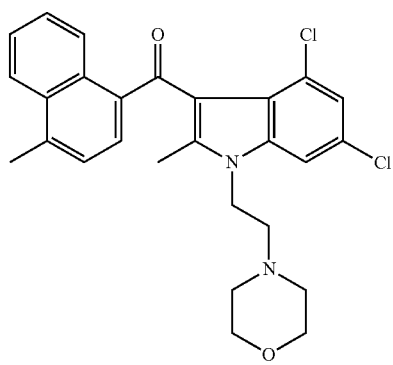 [SMILES: Cc1ccc(C(=O)c2c(C)n(CCN3CCOCC3)c3cc(Cl)cc(Cl)c23)c2ccccc12]

(4,6-dichloro-2-methyl-1-(2-morpholino ethyl)-1H-indol-3-yl)(4-methylnaphthalen-1-yl)methanone (CBX007)

To a solution of 4-methyl-1-naphthoyl chloride (29 mg, 0.14 mmol) and 4-(2-(4,6-dichloro-2-methyl-1H-indol-1-yl)ethyl)morpholine (44 mg, 0.14 mmol) in 1 mL $CH_2Cl_2$ at −70° C. was added dropwise ethyl aluminum dichloride (0.17 mL, 0.31 mmol, 1.8 M in toluene). The reaction mixture was allowed to slowly warm to room temperature overnight. The reaction mixture was then partitioned between ethyl acetate and cold $H_2O$, and the aqueous layer extracted twice with ethyl acetate. The combined organic extract was washed successively with $H_2O$, 10% $K_2CO_3$, and brine, dried over $MgSO_4$, filtered, and concentrated in vacuo. The crude product was purified via silica gel chromatography using a gradient from 0 to 3% MeOH in $CH_2Cl_2$ to give CBX007 (50 mg, 0.10 mmol). $^1H$ NMR (500 MHz, $CDCl_3$, δ): 2.46 (s, 3H), 2.55 (t, J=4.4 Hz, 4H), 2.74 (t, J=6.9 Hz, 2H), 2.77 (s, 3H), 3.74 (t, J=4.5 Hz, 4H), 4.25 (t, J=6.9 Hz, 2H), 7.10 (d, J=1.7 Hz, 1H), 7.21 (d, J=7.4 Hz, 1H), 7.31 (d, J=1.6 Hz, 1H), 7.42 (d, J=7.3 Hz, 1H), 7.60-7.74 (m, 2H), 8.10 (d, J=7.7 Hz, 1H), 8.94 (d, J=8.2 Hz, 1H). $^{13}C$ NMR (500 MHz, $CDCl_3$, δ): 12.09, 20.60, 42.21, 54.54, 57.91, 67.28, 108.62, 116.44, 122.84, 123.78, 124.66, 125.62, 126.70, 126.93, 127.12, 128.03, 128.18, 131.09, 131.49, 133.51, 137.34, 137.57, 140.30, 142.76, 194.75. MS m/z 481.6 $[M+H]^+$.

Example 10

Synthesis of JWH-450

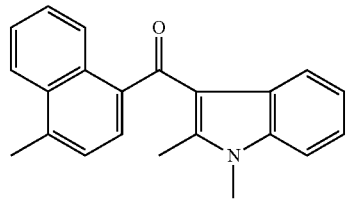 [SMILES: Cc1ccc(C(=O)c2c(C)n(C)c3ccccc23)c2ccccc12]

(1,2-dimethyl-1H-indol-3-yl)(4-methylnaphthalen-1-yl)methanone (JWH-450)

This compound was prepared according to the procedure outlined in Example 1.

Example 11

Cell Culture

All cell lines were grown at 5% $CO_2$ and 37° C. in cell culture growth media consisting of DMEM+GlutaMAX™-I (Gibco, Carlsbad, Calif.) supplemented with HEPES (10 mM), $NaHCO_3$ (5 mM), penicillin (100 U/ml)/streptomycin (00 μg/ml) and 10% FBS (heat-inactivated at 65° C. for 30 min) in 10 cm Falcon dishes (BD Biosciences, San Jose, Calif.). Cell maintenance consisted of media changes approximately every 3 days and when cells became 90% confluent, cells were trypsinized (1×0.25% Trypsin-EDTA, Glbco, Carlsbad, Calif.), resuspended in growth media and re-plated in cell culture dishes at a 1:10 dilution.

Generation of Stable HEK293 Cell Lines.

Stable $CB_1$ and $CB_2$ expressing HEK293 cell lines were generated using plasmids containing full coding region of mouse $CB_1$ and $CB_2$.

Fragments were amplified from total RNA of cell lines by reverse transcriptase-polymerase chain reaction (RT-PCR). Sequence was confirmed and the fragment was cloned into the EcoRI site of the pIRES2-eGFP-express vector. Cells were grown to approximately 80% confluence in 10 cm cell culture dishes, transfected with the cDNA pIRES-eGFP-vector containing the murine CB1 or CB2 receptor using LipofectAMINE™ 2000 reagent in the serum-free media Opti-MEM 1 according to the manufacturer's description. Cells were subject to FACS sorting 48 h after transfection and single cell sorted based on dsRed expression into 96-well plates. Of the dsRed expressing positive clones, 3 were validated for $CB_1$ and $CB_2$ protein expression by radioligand binding analysis (methods discussed below).

Example 12

Radioligand Binding
Membrane Protein Preparations for Radioligand Binding.

Cells were grown to 90% confluence, rinsed twice with 1×PBS and stored at −80° C. until further use. To prepare crude cellular membrane fractions, dishes were removed from −80° C. and thawed at room temperature for 5 min. Once thawed, cells were lysed with ice-cold homogenization buffer (50 mM Tris, 1 mM EDTA, 3 mM $MgCl_2$) and gently scraped from the dish. Total cell lysates from 3-5 dishes were collected on ice in 3 ml of ice-cold homogenization buffer. Cells were homogenized at 6,500 rpm (PRO Scientific, Oxford, Conn.) twice for 10 sec and centrifuged at 11,500 rpm for 20 min at 4° C. Supernatants were discarded and cell pellets were resuspended in homogenization buffer and triturated 10 times in ice-cold homogenization buffer. Crude cellular membrane homogenates were stored at −80° C. until further use. On the day of experiments, frozen homogenates were thawed at room temperature, gently triturated 10 times and subsequently dounce homogenized in a 7 ml glass tissue grinder (Wheaton Science Products, Millville, N.J.) by 5 strokes while on ice. The DC protein assay (BioRad, Hercules, Calif.) was utilized as instructed by the manufacturer to determine protein concentrations and BSA in homogenization buffer (see radioligand binding assay methods) was used for protein standards.

Radioligand Binding Assay.

Due to the lipophillic nature of the tested compounds, all experiments were performed in silanized glass test tubes (Altech, Deerfield, Ill.) with silanized pipette tips (VWR Scientific, Brisbane, Calif.) to reduce the loss of ligands. While on ice, the reaction components were added to the test tubes in the following order: 50 μl of non-radiolabeled ligand, 50 μl of radioligand and 100 μl of protein (50 μg) for a total reaction volume of 200 μl. The reactions were initiated with the addition of protein. Reactions did not contain greater than 0.1% DMSO. However, due to solubility limitations of some of the tested compounds, greater DMSO concentrations were used but controlled for in each experiment with the appropriate DMSO control. All components were prepared in binding buffer (50 mM Tris-base, 1 mM EDTA, 3 mM $MgCl_2$, 1 mg/ml BSA, pH=7.4) Once reactions were initiated, tubes were covered with parafilm and incubated in a water bath held at 30° C. with mild agitation for 1 hour. Reactions were stopped by adding ice-cold binding buffer under rapid filtration using the Brandel harvester (Brandel, Gaithersburg, Md.) and collected on Whatman GFB filter strips (Brandel, Gaithersburg Md.) that had been incubated in binding buffer for 1 h at room temperature. Filters were immediately transferred to 7 ml glass scintillation vials (VWR Scientific, Brisbane, Calif.) using the Brandel Manual Deposit (Brandel, Gaithersburg, Md.) and 5 ml scintillation fluid (National Diagnostics, Atlanta Ga.; Ecoscint XR) was added to each scintillation vial. Samples were rapidly vortexed for 10 sec, followed by 3 hour incubation at room temperature prior to obtaining radioactive counts in the scintillation counter (PerkinElmer, Boston Mass.). For radioligand saturation curves, [$^3$H]-CP95440 concentrations varied while using a constant saturating dose of a high-affinity non-radiolabeled ligand to determine non-specific binding. In radioligand competition experiments, [$^3$H]-CP95440 was held at the calculated $K_d$, ~1 nM, and the competing ligand concentrations varied. For competition binding assays, specific binding was calculated by subtracting the average dpm (disintegrations per minute, dpm) if non-specific points from the individual dpm values for each total binding point and expressed as either fmol/mg for saturation analyses or as a percent of total radioligand binding in competition curves. All experiments were performed in duplicate or triplicate, at a minimum of three different experiments.

Example 13

Cell Viability Assay

Cells were plated media supplemented with 10% serum in 96-well plates ($10^4$ cells per wellI; 0.1 ml per well). Once they reached ~70% confluence, they were rinsed with PBS and kept for an additional 24 hrs in media supplemented with 1% serum, at which time drugs or vehicle (DMSO, 0.1%, prepared in 10 μl serum-free media) were directly added to each well. After 3 days, cell viability was assessed using the Cell Proliferation Reagent WST-1 (Roche, Indianapolis, Ind.). Briefly, WST-1 reagent (10 μl) was added to each well for 3 hrs at 37° C. with 5% $CO_2$ and WST-1 products were read at 450 nm using Packard SpectraCount™.

Example 14

Quantitative RT-PCR

RNA was extracted using PerfectPure RNA Cultured Cell Kit (5 prime). Real-time quantitative PCR assays were performed using the Brilliant® II QRT-PCR Master Mix, 1-Step kit (Stratagene) and probes were obtained from the Universal Probe Library Set (Roche Applied Science). The following sense/antisense primers and probes were used: human $CB_1$: 5'-TGTCTGTCTGCACACCTTGAA-3' and 5'-CATCTG-CACATGACAGAGAGG-3', probe #40; human $CB_2$: 5'-TGGGAGAGGACAGAAAACAACT-3' and 5'-GAGCT-TGTCTAGAAGGCTTTGG-3', probe #24; human GPR124 5'-GGCTCCTTCCTGGGACTG-3' and 5'-GCACTGTGCT-GATGATGTTGT-3' probe #67; mouse GPR124 5'-GTC-CCTGTTGGAGAAGTTGG-3' and 5'-AGCGTTT-TAGCTCTCTCCCAGA-3', probe #1. Universal ProbeLibrary Human HPRT Gene Assays (Roche Applied Science) were used as references in dual color qPCR reactions Amplifications were run in a Mx3000P™ Real-Time PCR System (Stratgene).

Example 15

Data Analysis

All data were analyzed using the GraphPad PRISM® 4.02 program (GraphPad Software, San Diego, Calif.). Data from radioligand binding experiments were calculated as follows: the average dpm values of the non-specific points were subtracted from each individual total dpm values. For saturation analyses, the calculated specific binding values were expressed as fmol/mg and graphed against the free concentrations of [$^3$H]-CP55940. All radioligand competition binding values were normalized by expressing values as a percent of the maximal amount of radioligand displaced by a non-radiolabeled compound in each cell line. All data is represented as a mean±SEM. Statistical analyses were performed using GraphPad PRISM® 4.02.

Example 16

Design of a Genetic Approach to Identify the Gene Encoding for AAI Receptors

1: Select Cells Lacking $CB_1/CB_2$ Receptors:

The expression level of $CB_1$ and $CB_2$ mRNA is determined by qPCR in eight human cell lines and found three, T98g, MDA231 and sknmc cells, that lack $CB_1$ and $CB_2$ mRNA (Table 1).

TABLE 1

| human cell lines | CB1, ΔCt | CB2, ΔCt |
|---|---|---|
| T98G | no ct | no ct |
| MDA231 | no ct | no ct |
| sknmc | no ct | no ct |
| SW480 | 8.29 | no ct |
| SF767 | 11.11 | no ct |
| HT29 | 13.41 | no ct |
| U87 | 7.73 | no ct |
| hek | 10.13 | no ct |
| U3t3 cDNA | −5.22 | no ct |
| HL60 cDNA | 6.37 | −3.49 |

2. Determine the Sensitivity Profile of $CB_1/CB_2$—KO Cells to WIN55212-2:

WIN55212-2 has been shown to kill tumor cells in culture independently of $CB_1/CB_2$ receptors. Based on this evidence, it was determined if WIN55212-2 differentially kills T98g, MDA231 and sknmc cells, which provides an index of AAI receptor functionality in these cells. Also tested is $\Delta^9$-THC (classic cannabinoid) and CP55940 (non-classical cannabinoid).

The potency of WIN55212-2 at killing T98g, MDA231 and sknmc cells was within similar micromolar ranges (1.5-2.9 μM) and exhibited gradual toxic efficacy (T98g>MDA>sknmc) (FIG. 1). Conversely, both THC and CP55940 exhibited inconsistent potencies and efficacies at killing these cells, suggesting that T98g, MDA231 and sknmc cells express AAI receptors at different expression levels, and that AAI compound induces the strongest toxic response in the human astrocytoma cell line T98g.

Figure 2:
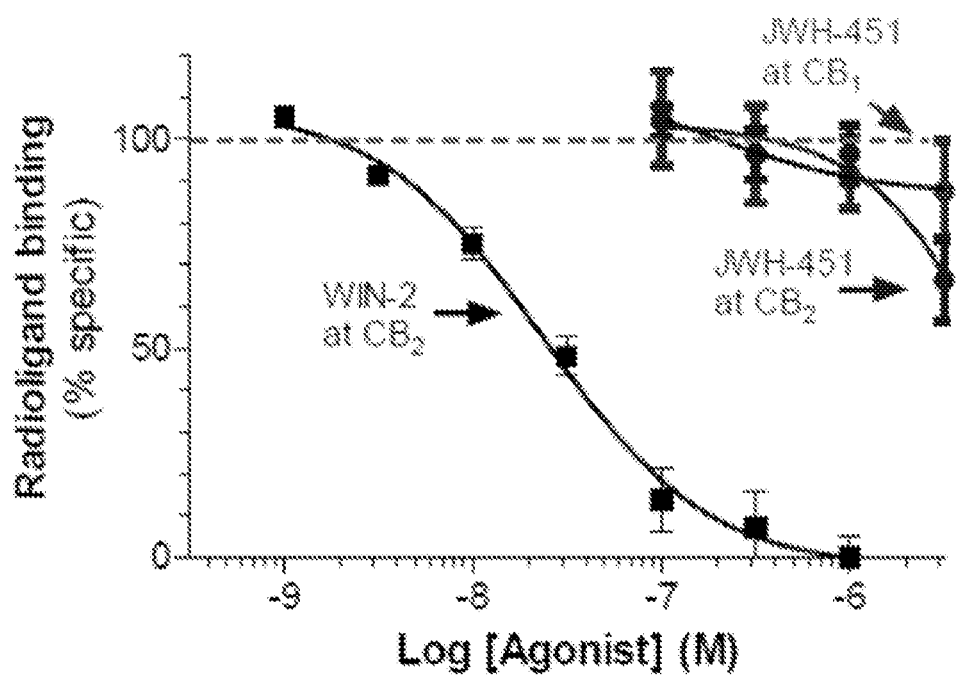
FIG. 2 shows WIN-2 competes for [$^3$H]-CP55940 binding at $CB_1$ (not shown) and $CB_2$ (squares); whereas JWH-451 does not (circles).

3: SAR Study and Optimization of AAI Compounds:

Because the strongest toxic effect of WIN55212-2 was measured in T98g cells, these cells are used as readout to study the structure activity relationship (SAR) of AAI compounds at inducing cell death through AAI receptors. Table 2 provides the toxic potency and efficacy of 16 rationally-selected AAI compounds. JWH-451 induced the optimal combination of highest potency (1.1 μM) and high efficacy (kills 81% of the cells). JWH-451 also exhibited 100 fold lower affinity at $CB_1$ and $CB_2$ receptors than WIN55212-2, making it the first ligand at AAI receptors exhibiting reduced affinity at $CB_1/CB_2$ receptors as compared to WIN55212-2 (FIG. 2).

TABLE 2

| Compound | Structure | Toxic potency at T98g cells potency μM (percent efficacy) |
|---|---|---|
| WIN55212-2 (commerically available) | 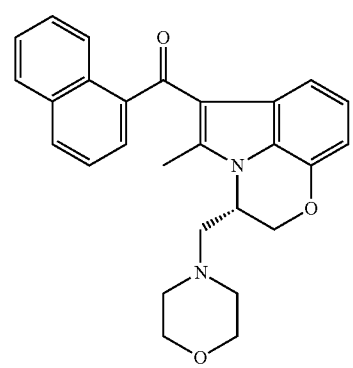 [SMILES: Cc1c(C(=O)c2cccc3ccccc23)c2cccc3c2n1[C@@H](CN1CCOCC1)CO3] | 1.5 μM (87%) |
| Pravadoline (commerically available) | 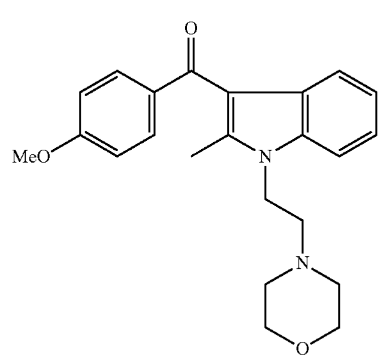 [SMILES: COc1ccc(C(=O)c2c(C)n(CCN3CCOCC3)c3ccccc23)cc1] | 22 μM (88%) |

TABLE 2-continued

| Compound | Structure | Toxic potency at T98g cells potency μM (percent efficacy) |
|---|---|---|
| JWH-451 | 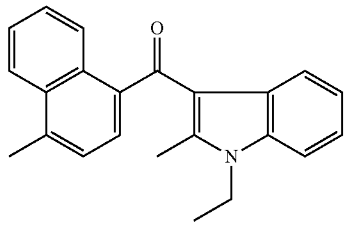 [SMILES: CCn1c(C)c(C(=O)c2ccc(C)c3ccccc23)c2ccccc21] | 1.1 μM (81%) |
| JWH-450 | 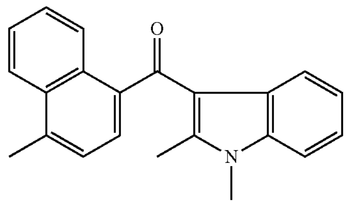 [SMILES: Cc1ccc(C(=O)c2c(C)n(C)c3ccccc23)c2ccccc12] | 2 μM (66%) |
| TK-18 | 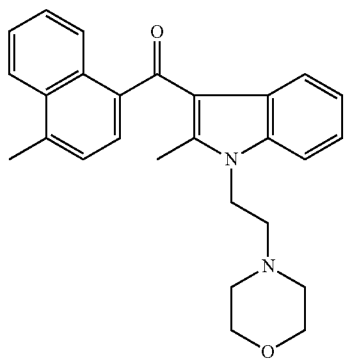 [SMILES: Cc1ccc(C(=O)c2c(C)n(CCN3CCOCC3)c3ccccc23)c2ccccc12] | 3 μM (48%) |
| CBX-002 | 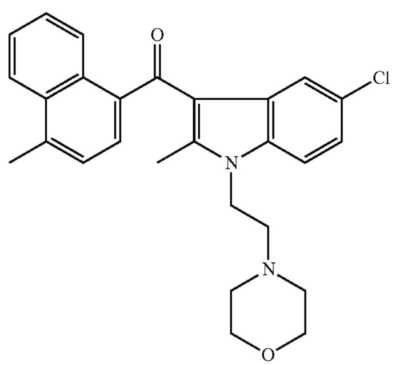 [SMILES: Cc1ccc(C(=O)c2c(C)n(CCN3CCOCC3)c3ccc(Cl)cc23)c2ccccc12] | 30 μM (45%) |
| CBX-004 | 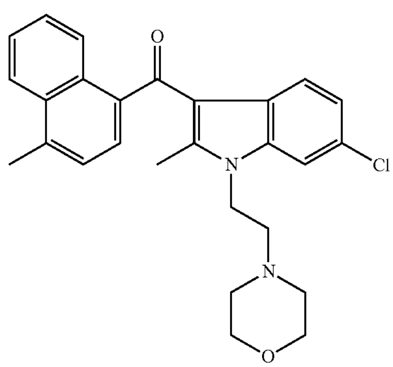 [SMILES: Cc1ccc(C(=O)c2c(C)n(CCN3CCOCC3)c3cc(Cl)ccc23)c2ccccc12] | 2 μM (68%) |

TABLE 2-continued

| Compound | Structure | Toxic potency at T98g cells potency μM (percent efficacy) |
|---|---|---|
| CBX-003 | 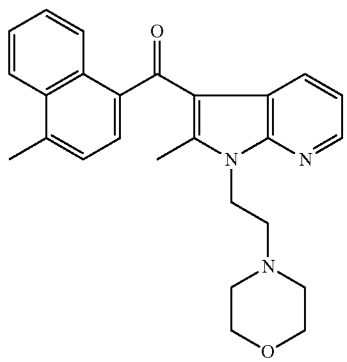 [SMILES: Cc1ccc(C(=O)c2c(C)n(CCN3CCOCC3)c3ncccc23)c2ccccc12] | 5 μM (71%) |
| CBX-005 | 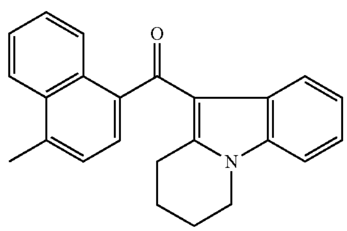 [SMILES: Cc1ccc(C(=O)c2c3n(c4ccccc24)CCCC3)c2ccccc12] | 1.2 μM (64%) |
| CBX-007 | 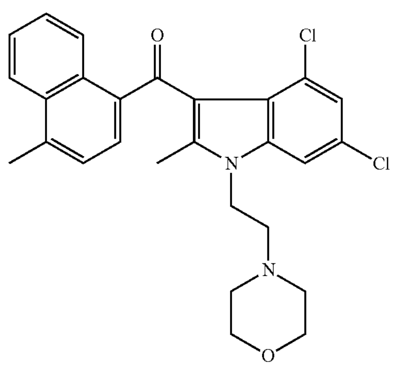 [SMILES: Cc1ccc(C(=O)c2c(C)n(CCN3CCOCC3)c3cc(Cl)cc(Cl)c23)c2ccccc12] | 0.6 μM (56%) |
| JWH-015 (commerically available) | 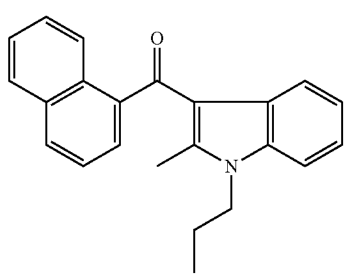 [SMILES: CCCn1c(C)c(C(=O)c2cccc3ccccc23)c2ccccc21] | 1.3 μM (58%) |
| JWH-042 (Drug and Alcohol Dependence, 2000. 60(2): p. 133-140) | 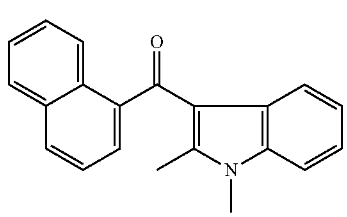 [SMILES: Cc1c(C(=O)c2cccc3ccccc23)c2ccccc2n1C] | 3.1 μM (71%) |

TABLE 2-continued

| Compound | Structure | Toxic potency at T98g cells potency μM (percent efficacy) |
|---|---|---|
| JWH-043 (Drug and Alcohol Dependence, 2000. 60(2): p. 133-140) | 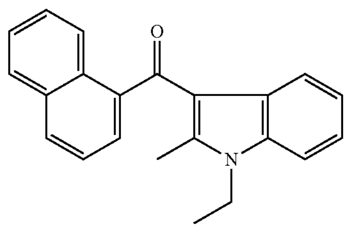 [SMILES: CCn1c(C)c(C(=O)c2cccc3ccccc23)c2ccccc21] | 6.9 μM (84%) |
| JWH-148 (Reggio, P. H. (ed.) The cannabinoid receptors. Humana Press, Totowa, NJ 2008. p. 49-94.) | 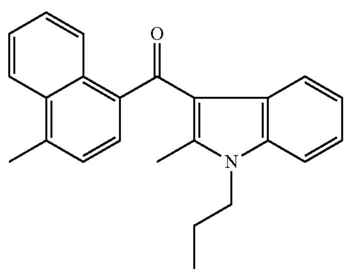 [SMILES: CCCn1c(C)c(C(=O)c2ccc(C)c3ccccc23)c2ccccc21] | 2 μM (48%) |
| TK-8 (commerically available) | 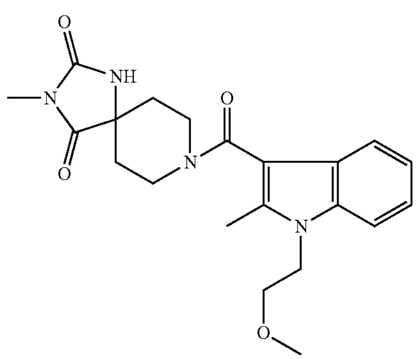 [SMILES: COCCn1c(C)c(C(=O)N2CCC3(CC2)NC(=O)N(C)C3=O)c2ccccc21] | 886 μM (55%) |
| TK-2 (commerically available) | 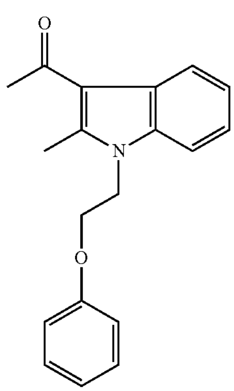 [SMILES: CC(=O)c1c(C)n(CCOc2ccccc2)c2ccccc12] | 3.1 μM (81%) |

TABLE 2-continued

| Compound | Structure | Toxic potency at T98g cells potency μM (percent efficacy) |
|---|---|---|
| TK-15 (commerically available) | 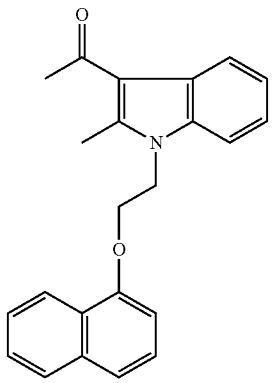 [SMILES: CC(=O)c1c(C)n(CCOc2cccc3ccccc23)c2ccccc12] | 45 μM (62%) |
| TK-14 (commerically available) | 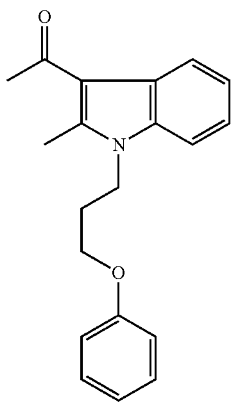 [SMILES: CC(=O)c1c(C)n(CCCOc2ccccc2)c2ccccc12] | 40 μM (92%) |
| JWH-200 (commerically available) | 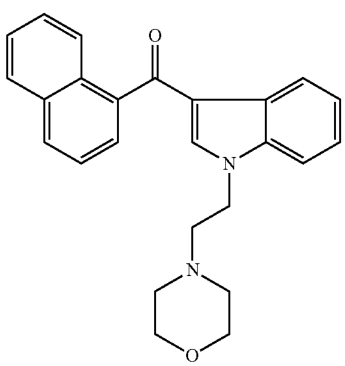 [SMILES: O=C(c1cccc2ccccc12)c1cn(CCN2CCOCC2)c2ccccc12] | 21 μM (48%) |
| AM630 (commerically available) | 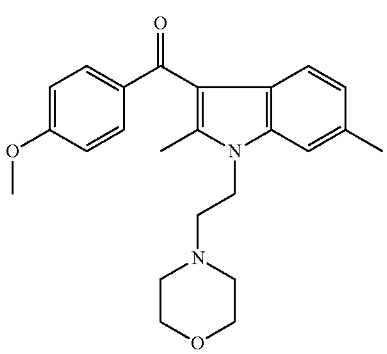 [SMILES: COc1ccc(C(=O)c2c(C)n(CCN3CCOCC3)c3cc(C)ccc23)cc1] | 7.8 μM (92%) |

The SAR of AAI compounds at killing T98g cells through AAI receptors was further focused by results showing that thirteen additional analogues of WIN55212-2 and JWH-451, each holding distinct chemical moieties, did not affect the viability of T98g cells (Table 3.)

TABLE 3

| Compound | Structure | Activity at killing T98g cells percent efficacy at 10 μM |
| --- | --- | --- |
| JWH-120 (Drug and Alcohol Dependence, 2000. 60(2): p. 133-140) | 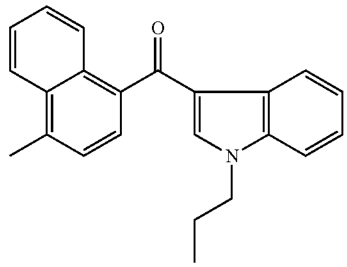 [SMILES: CCCn1cc(C(=O)c2ccc(C)c3ccccc23)c2ccccc21] | 0% |
| JWH-370 | 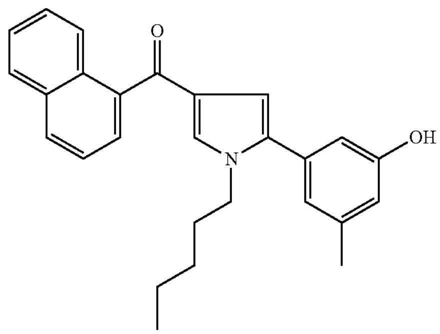 [SMILES: CCCCCn1cc(C(=O)c2cccc3ccccc23)cc1-c1cc(C)cc(O)c1] | 11% |
| TK10 (comerically available) | 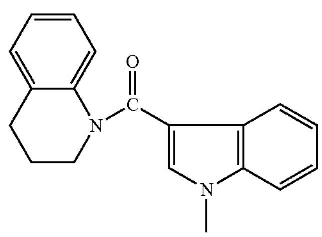 [SMILES: Cn1cc(C(=O)N2CCCc3ccccc32)c2ccccc21] | 0% |
| TK4 (comerically available) | 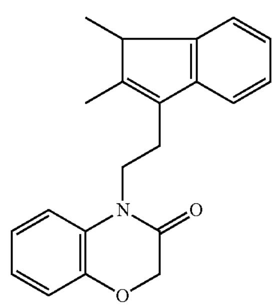 [SMILES: CC1=C(CCN2C(=O)COc3ccccc32)c2ccccc2C1C] | 10% |
| TK11 (comerically available) | 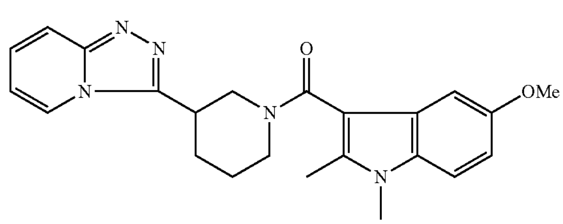 [SMILES: COc1ccc2c(c1)c(C(=O)N1CCCC(c3nnc4ccccn34)C1)c(C)n2C] | 10% |

TABLE 3-continued
| Compound | Structure | Activity at killing T98g cells percent efficacy at 10 μM |
|---|---|---|
| TK12 (comerically available) | 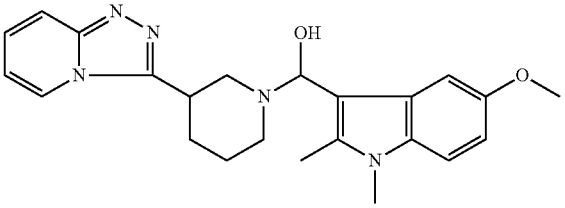 [SMILES: COc1ccc2c(c1)c(C(O)N1CCCC(c3nnc4ccccn34)C1)c(C)n2C] | 16% |
| TK3 (comerically available) | 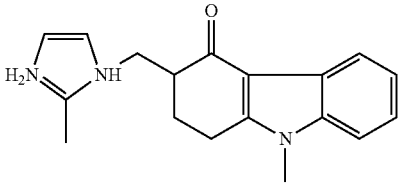 [SMILES: Cc1nccn1CC1CCc2c(c3ccccc3n2C)C1=O] | 11% |
| TK6 (comerically available) | 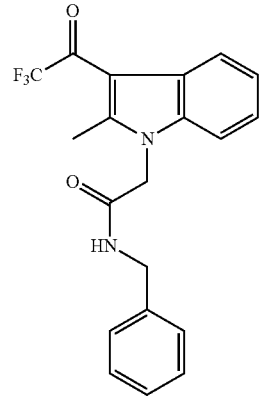 [SMILES: Cc1c(C(=O)C(F)(F)F)c2ccccc2n1CC(=O)NCc1ccccc1] | 8% |
| TK9 (comerically available) | 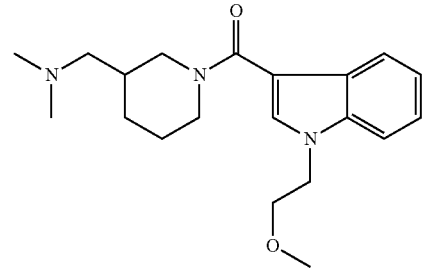 [SMILES: COCCn1cc(C(=O)N2CCCC(CN(C)C)C2)c2ccccc21] | 0% |
| TK5 (comerically available) | 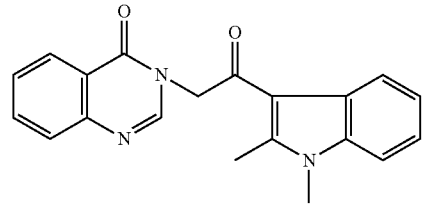 [SMILES: Cc1c(C(=O)Cn2cnc3ccccc3c2=O)c2ccccc2n1C] | 3% |

TABLE 3-continued

| Compound | Structure | Activity at killing T98g cells percent efficacy at 10 μM |
|---|---|---|
| TK16 (comerically available) | [structure: 3-benzoyl-2-methyl-1-(2-morpholino-2-oxoethyl)indole] | 3% |
| TK7 (comerically available) | [structure: 9-benzyl-2,3-dihydro-1H-carbazol-4(9H)-one] | 19% |
| TK-1 (comerically available) | [structure: N-((1,4,5-trimethyl-1H-pyrazol-3-yl)methyl)morpholin-4-amine] | 6% |

4: Identification of Gene Candidates for AAI Receptors:

Since evidence suggest that AAI receptor couple to G proteins, gene array analysis of T98g, MDA231 and skmnc cells was performed focusing to mRNA that encode for GPCRs. Gene arrays were generated by pooling total mRNA extracted from three independent cultures for each cell line. All three cell lines expressed 39 GPCR mRNAs in common. These 39 genes represent gene candidates:

| | | | | | | |
|---|---|---|---|---|---|---|
| GPR1 | GPR126 | GPR18 | GPR25 | GPR45 | GPR124 | GPR85 |
| GPR116 | GPR135 | GPR19 | GPR37 | GPR50 | GPR64 | GPR97 |
| GPR12 | GPR144 | GPR20 | GPR39 | GPR52 | GPR65 | |
| GPR124 | GPR17 | GPR21 | GPR4 | GPR56 | GPR68 | |
| GPR125 | GPR173 | GPR22 | GPR44 | GPR6 | GPR75 | |

Figure 3:
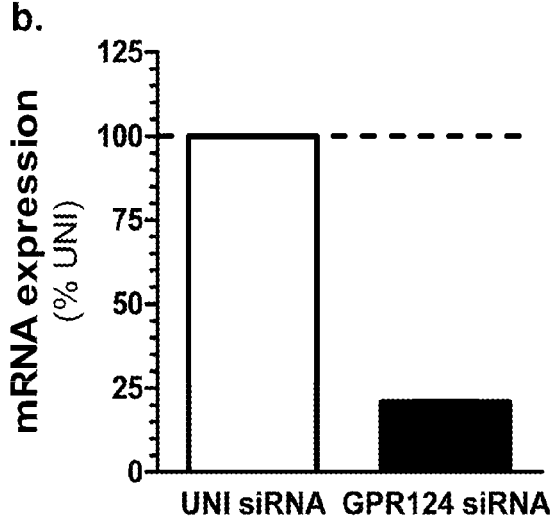
FIG. 3 shows siRNA indentification (following the decline of mRNA over 4 days in vitro to ascertain for knockdown stability). Sequence homology between $CB_2$ and GPR124 within the $3^{rd}$ transmembrane domain, which contains an interaction site for WIN binding to $CB_2$ receptors.
Figure 3:
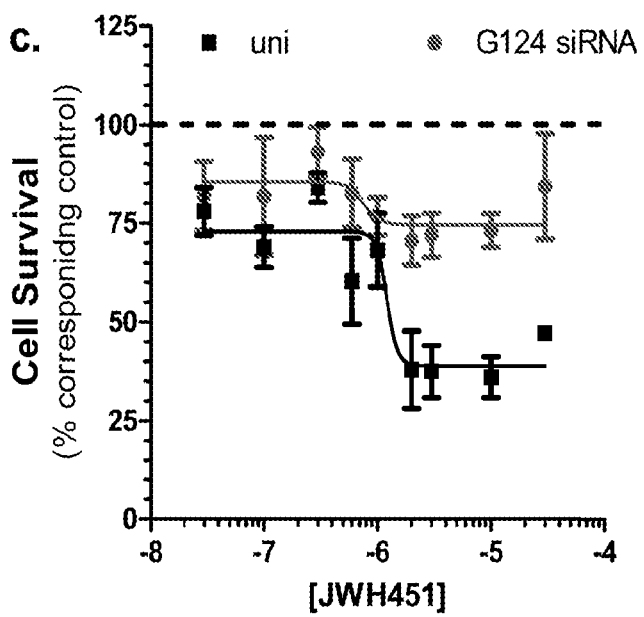

5: Identification of GPR124 as an AAI Receptor:

To determine which of the gene candidate encodes for AAI receptors, an siRNA approach is used to knock down each candidate individually to determine which one prevents the toxic effect of JWH-451 and thus encodes for AAI receptors. The prediction is that knocking down AAI receptors prevents the cell death induced by JWH-451. T98g cells were treated with siRNA targeting each of the 39 GPCR gene candidates individually. The first experiment was designed to knock down each GPCR candidate using a mixture of 3 siRNAs thus maximize genetic targeting efficacy. Thus, cells were incubated with siRNA mixtures and then treated with JWH-451 (1 μM) and cell viability measured after three days. Only one mixture of siRNAs (that targeting GPR124) decreased the toxicity of JWH-451. To validate this result, the mixture of 3 siRNA targeting GPR124 was deconvulted by testing each siRNA separately, measuring their respective efficacy at knocking down GPR124 mRNA by qPCR. Two of the three siRNAs knocked-down GPR124 expression by more than 80% over 4 days (FIG. 3b). FIG. 3c shows the results obtained with one of these siRNA, demonstrating that the JWH-451-induced killing of T98g cells is reduced when GPR124 mRNA expression is concomitantly reduced. The killing effect induced by JWH-451 is mediated by GPR124, a AAI receptor.

When comparing the overall amino acid sequence of GPR124 to that of $CB_1$ and $CB_2$ receptors no significant homology was found. However, when focusing the comparison to the amino acid sequence encoding for the $3^{rd}$ transmembrane domains of GPR124 and $CB_2$ receptors, 84% homology was found (FIG. 3a). Site directed mutagenesis studies show that WIN55212-2 interacts directly with the $3^{rd}$ transmembrane domain of $CB_2$ receptors. Therefore, it is likely that WIN55212-2, JWH-451 and other AAI compound interact directly with the $3^{rd}$ transmembrane domain of GPR124.

Example 17

Toxic Profile of JWH-451

Figure 4:
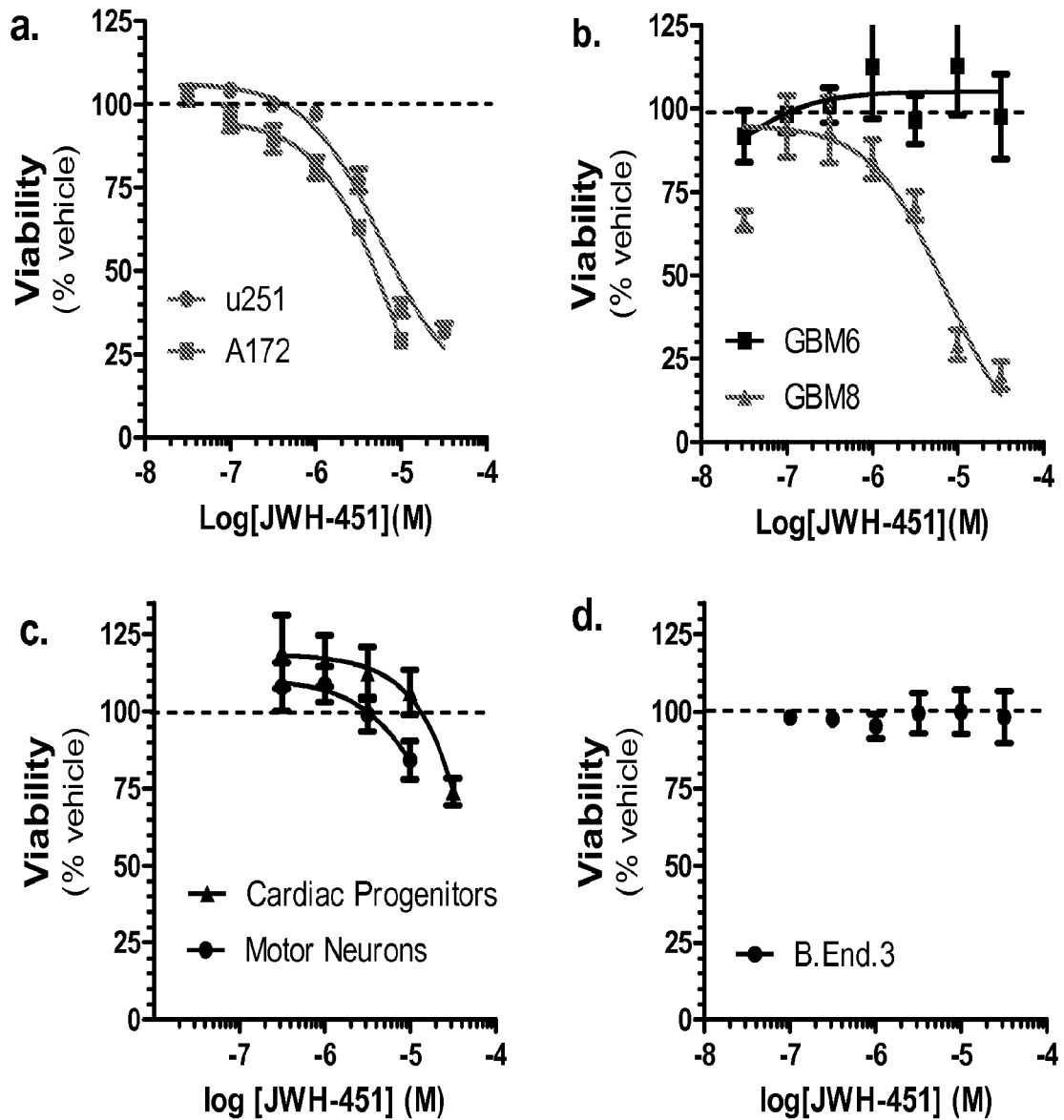
FIG. 4 shows JWH-451 toxic potency on different cell types.

JWH-451 was tested for toxicity in cells expressing GPR124. JWH-451 was equipotent at killing human astrocytoma cell lines: U251, A172 and GBM8 (potencies of 2-4 μM, FIG. 4); JWH-451 exhibited much less toxic effect on cardiac and motorneuron progenitors; and did not affect the viability of mouse neurons in primary culture and the endothelial cell line bEnd.3. Thus, JWH-451 efficaciously kills malignant cells, does not significantly affect the viability of progenitor cells and healthy non-malignant cells.

In Vivo Profile of JWH-451

Figure 5:
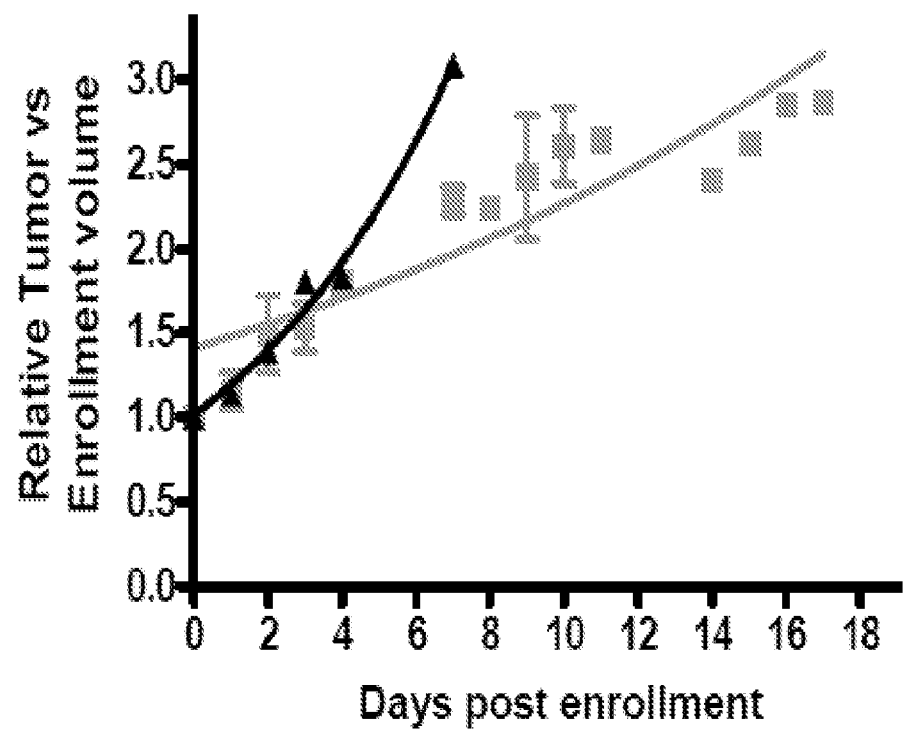
FIG. 5 shows daily i.p. injections of JWH-451 (5 mg/Kg, squares) inhibits the growth of U251 gliomas implanted in the flanks of nude mice, as compared to controls (triangles).

Nude mice that had been implanted with U251 flank tumors were treated with a daily regimen of JWH-451. This experiment was performed as follow: $10^6$ U251 cells were implanted in the flanks of nude mice and the tumor was allowed to grow until it reached a size of 250 $mm^3$, at which point the mice were enrolled in daily treatment. Tumor growth was then measured and expressed as a function of initial tumor size. Daily i.p. injection of JWH-451 (15 mg/Kg) significantly reduced tumor growth in vivo (FIG. 5).

Example 18

JWH-451 Formulation and Pharmacokinetic

A liposome formulation composed of phosphatidylcholine:PEG (6:1) that keeps JWH-451 soluble in 4° C. buffer for two weeks is prepared.

Figure 6:
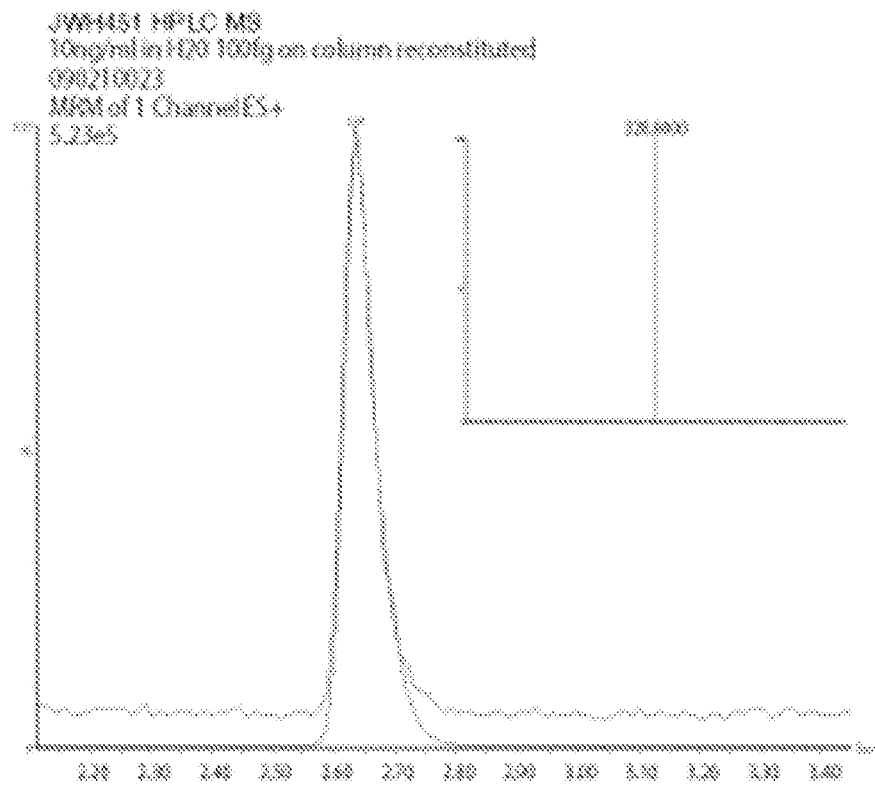
FIG. 6 shows LC-MS chromatogram of JWH-451 detected in mouse brain and the levels reached one hour following i.p. injection of 5, 15 and 40 mg/Kg of JWH-451.
Figure 6:
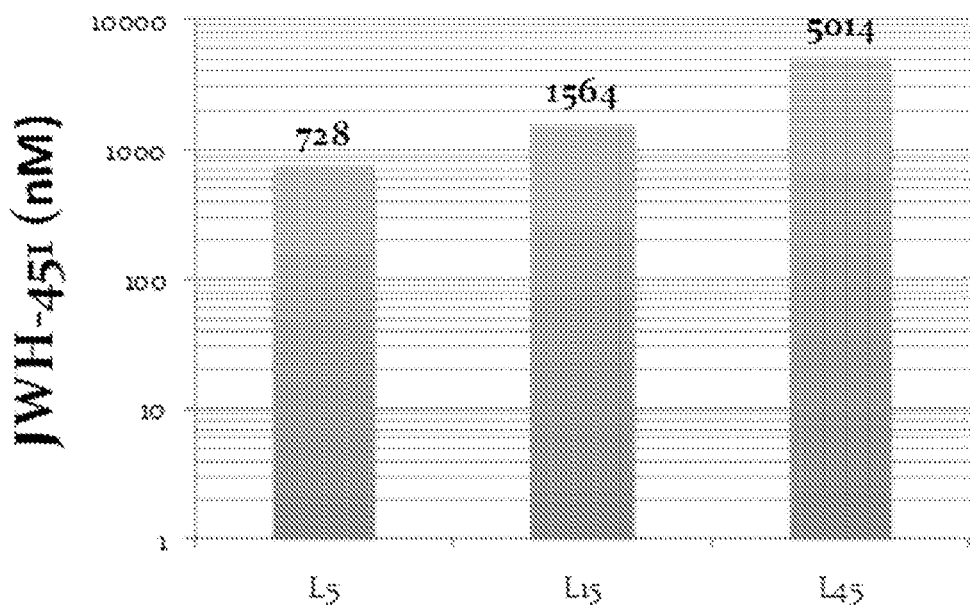

Initial pharmacokinetic (PK) evaluations indicate that formulated JWH-451 injected to mice (i.p.) at 5, 15 and 45 mg/Kg results after one hour in JWH-451 reaching concentrations of 0.7-1, 1.5-2.2 and 3.7-5 μM, respectively, in mouse brain and blood (FIG. 6) Here, levels of JWH-451 in tissue were quantified by LC-MS, using JWH-015 ((2-methyl-1-propyl-1H-indol-3-yl)(naphthalen-1-yl)methanone) as LC-MS standard and generating external calibration curves. These PK results show that injecting formulated JWH-451 peripherally lead to JWH-451 concentrations in mouse brain and blood that are within the range of efficacious GPR124 activation to kill astrocytomas.

Example 19

Lymphocyte Invasion In Vivo

Effect of JWH-451 on the immune cell invasion of syngenic mouse model of astrocytomas tumors (mouse astrocytoma cell implanted into the brain of wild type mice hosts with intact immune systems) was measured. Briefly, mice (BALB/c, 8 week-old, male, Charles River) were used for this study and housed under specific-pathogen-free conditions for at least one week prior to surgery. Twenty-four hours before surgery, $5 \times 10^6$ DBT cells were harvested in 10 ml of DMEM supplemented with 10% heat-inactivated FBS, 10 U/ml penicillin and 10 μg/ml streptomycin and seeded in T75 $cm^2$ cell culture flasks (one flask per mouse). Just before surgery, cells from one flask were detached with trypsin-EDTA, recovered in DMEM supplemented with 10% heat-inactivated FBS, centrifuged/rinsed twice with MEM (serum free) and resuspended at $10^6$ cells/ul of ice-cold MEM (ready for injection). Mice were anesthetized with ketamine/xylazine (given 0.1 ml per gram body weight i.p., 130 mg/kg ketamine/8.8 mg/kg xylazine) and placed in a stereotactic instrument (David Kopf Instruments, CA) on an isothermal pad (Deltaphase®, Braintree Scientific, Inc, Braintree, Mass.). After midline incision of the scalp, a 25-G needle was used to perform a craniostomy at 2 mm cranial from bregma and 1.5 mm left lateral. Another 25-G needle containing the cells was then lowered 2 mm into the cortex through the craniostomy and 1 μl containing $10^6$ DBT cells was injected over 3 min using a microinjector (Life Sciences Instruments, CA). The needle was kept in place for 2 min after injection and then removed slowly, followed by gentle irrigation with 0.9% saline to flush residual cells. The craniostomy and scalp were closed with bonewax (Ethicon, N.J.) and silk suture (no. 3-0, Ethicon), respectively. Anesthesia was reversed with yohimbine and animals were allowed to recover on the heating pad. Three weeks after tumor implantation, mice were euthanized by pentobarbital overdose, transcardially-perfused with 25 ml of cold PBS, followed by 25 ml of paraformaldehyde (PFA, 4%). Brains were removed and placed in PFA (4%) overnight, followed by sucrose (30% in PBS, 4° C., until the sample sunk). Brains were then embedded in Tissue Tek O.C.T. media (Sakura, Calif.), snap frozen in 2-methylbutane chilled in liquid nitrogen for 30 sec and stored at −80° C. Coronal sections (4 μm) were cut using a cryostat (Reichert-Jung 2800 Frigocut E), air-dried and fixed in ethanol (70% for 1 min), followed by one rinse with water and staining with haematoxylin-eosin (5 sec in concentrated Mayer's hematoxylin and 60 sec in concentrated Eosin Y).

Figure 7:
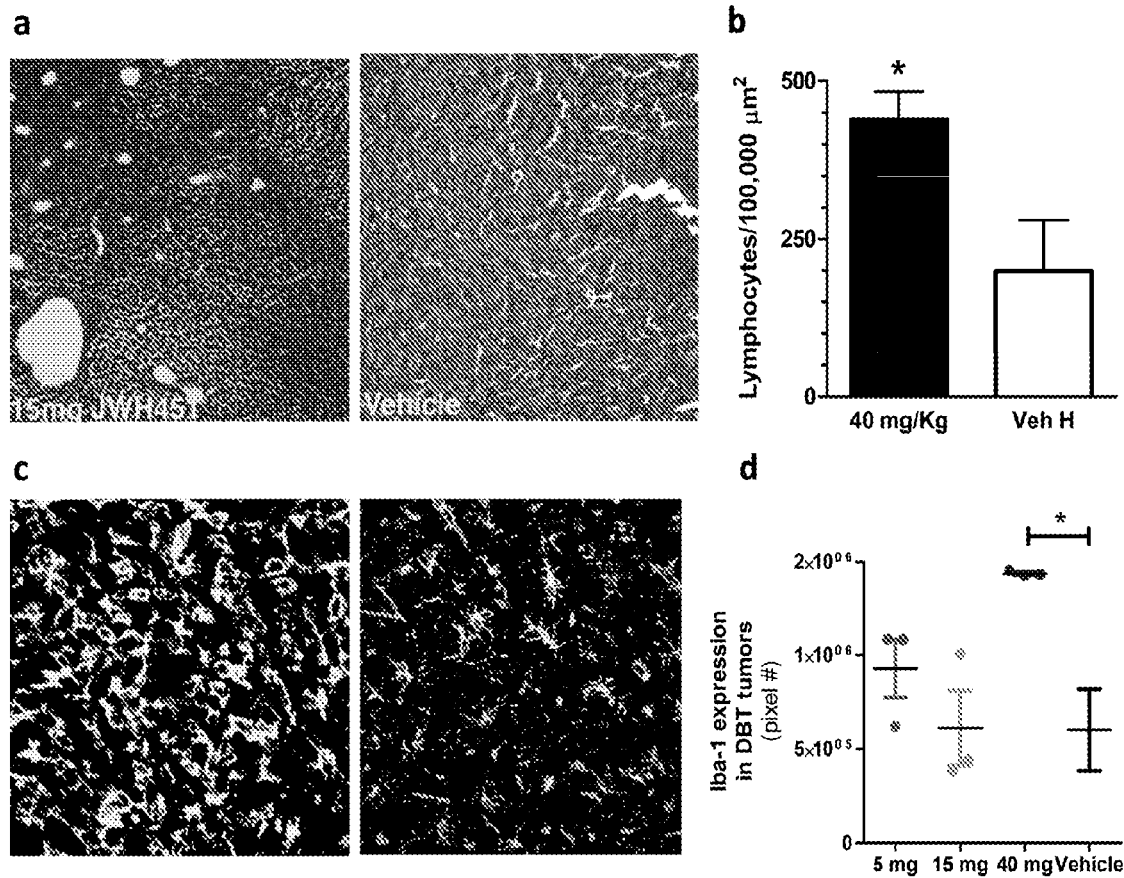
FIG. 7 shows quantification of lymphocytes and brain macrophage density using H&E and Iba-1 IHC stained sections harvested from mouse DBT tumors implanted for three weeks in mouse brain. Daily treatment with JWH-451 (40 mg/Kg; i.p.) led to a two fold increase in lymphocyte and brain macrophage density within the tumor core.

Daily i.p. injection of formulated JWH-451 leads to a two fold increase in the number of both lymphocytes and brain macrophages invasion of DBT tumors (FIG. 7), suggesting that part of the therapeutic mechanism of action of JWH-451 at killing astrocytomas is to render that blood brain barrier leakier to invading lymphocytes and brain macrophages, possibly boosting an immune response against tumors.

The disclosures of all articles and references mentioned in this application, including patents, are incorporated herein by reference in their entirety.

It is understood that the examples and embodiments described herein are for illustrative purposes only. Unless clearly excluded by the context, all embodiments disclosed for one aspect of the invention can be combined with embodiments disclosed for other aspects of the invention, in any suitable combination. It will be apparent to those skilled in the art that various modifications and variations can be made to the present invention without departing from the scope of the invention. Thus, it is intended that the present invention cover the modifications and variations of this invention provided they come within the scope of the appended claims and their equivalents. All publications, patents, and patent applications cited herein are hereby incorporated herein by reference for all purposes.

What is claimed is:

1. A compound of formula:

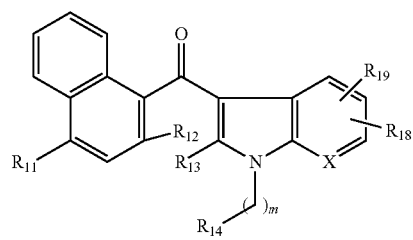

or pharmaceutically acceptable salts, wherein
X is CH or N;

$R_{11}$ is $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, halogen, —$NO_2$, —CN, —$OR_{15}$, or —$NR_{16}R_{17}$, each being optionally substituted with one to four $R_{20}$;

$R_{12}$ is H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, halogen, —$NO_2$, —CN, —$OR_{15}$, or —$NR_{16}R_{17}$, each being optionally substituted with one to four $R_{20}$;

$R_{14}$ and $R_{13}$ taken together with the atoms to which they are attached form a 5-, 6-, or 7-membered heterocyclyl group optionally substituted with one to four $R_{20}$;

$R_{15}$, $R_{16}$, and $R_{17}$ are independently H, $C_1$-$C_6$ alkyl, $C_2$-$C_6$ alkenyl, or $C_2$-$C_6$ alkynyl $R_{18}$ and $R_{19}$ are each independently H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, halogen, —$NO_2$, —CN, —$OR_{15}$, or —$NR_{16}R_{17}$, each being optionally substituted with one to four $R_{20}$, $R_{20}$ is halogen, —CN, —OH, —$NO_2$, —$NH_2$, —NH($C_1$-$C_6$ alkyl), —N($C_1$-$C_6$ alkyl)$_2$, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ alkoxy, or $C_1$-$C_6$ haloalkoxy; and m is an integer 1 or 2.

2. The compound according to claim 1, wherein X is CH.

3. The compound according to claim 1, wherein $R_{11}$ is $C_1$-$C_6$ alkyl or $C_1$-$C_6$ alkoxy.

4. The compound according to claim 3, wherein $R_{11}$ is methyl or methoxy.

5. The compound according to claim 1, wherein $R_{12}$ is H.

6. The compound according to claim 1, wherein $R_{13}$ and $R_{14}$ taken together with the atoms to which they are attached form a 6-membered heterocyclyl optionally substituted with one to four $R_{20}$.

7. The compound according to claim 1, wherein $R_{18}$ and $R_{19}$ are each independently H, $C_1$-$C_6$ alkoxy, $C_1$-$C_6$ haloalkoxy, halogen, or —OH.

8. The compound according to claim 1, which is:

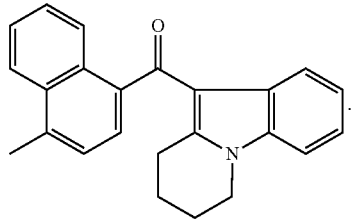 [SMILES: Cc1ccc(C(=O)c2c3n(c4ccccc24)CCCC3)c2ccccc12]

9. A pharmaceutical composition comprising a therapeutically effective amount of a compound according to claim 1 and one or more pharmaceutically acceptable diluents, preservatives, solubilizers, emulsifiers, adjuvants, excipients, or carriers.

10. The compound according to claim 1, wherein $R_{12}$ is H or $C_1$-$C_6$ alkyl optionally substituted with $R_{20}$.

* * * * *